US012002151B2

(12) United States Patent
Valine

(10) Patent No.: US 12,002,151 B2
(45) Date of Patent: *Jun. 4, 2024

(54) GRAPHICAL DISPLAY OF VOLUME OF ACTIVATION

(71) Applicant: Medtronic, Inc., Minneapolis, MN (US)

(72) Inventor: Lukas Valine, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/664,350

(22) Filed: May 20, 2022

(65) Prior Publication Data

US 2022/0351462 A1 Nov. 3, 2022

Related U.S. Application Data

(63) Continuation of application No. 16/733,936, filed on Jan. 3, 2020, now Pat. No. 11,341,717.

(51) Int. Cl.
*G06T 15/80* (2011.01)
*G06T 1/20* (2006.01)
*G06T 17/20* (2006.01)

(52) U.S. Cl.
CPC ............... *G06T 15/80* (2013.01); *G06T 1/20* (2013.01); *G06T 17/205* (2013.01); *G06T 2200/24* (2013.01); *G06T 2210/41* (2013.01)

(58) Field of Classification Search
CPC ......... G06T 15/80; G06T 1/20; G06T 17/205; G06T 2200/24; G06T 2210/41; A61N 1/37241; A61N 1/37247
See application file for complete search history.

(56) References Cited

U.S. PATENT DOCUMENTS

| 8,380,321 B2 | 2/2013 | Goetz et al. |
| 9,861,821 B2 | 1/2018 | Kaemmerer |
| 9,993,649 B2 | 6/2018 | Astrom et al. |
| 11,341,717 B2 | 5/2022 | Valine |
| 2004/0125103 A1* | 7/2004 | Kaufman ................ G06T 15/08 345/419 |

(Continued)

FOREIGN PATENT DOCUMENTS

| EP | 3471821 A1 | 4/2019 |
| WO | 2017216372 A1 | 12/2017 |

OTHER PUBLICATIONS

"Marching Cubes or something else?", accessed from https://www.gamedev.net/forums/topic/574042-marching-cubes-or-something-else/, uploaded by user bbtrb, Tom, posted online Jun. 14, 2010, 3 pp.

(Continued)

*Primary Examiner* — Michael Le
(74) *Attorney, Agent, or Firm* — Shumaker & Sieffert, P.A.

(57) ABSTRACT

The disclosure is directed to rendering visual representations of VOAs by manipulating vertices of a three-dimensional (3-D) mesh structure. In one example, a processing circuitry of a computing device may receive a 3-D mesh structure having adjustable vertices. The processing circuitry may adjust the vertices to generate an adjusted shape of the 3-D mesh structure according to an intersection between activated tissue and non-activated tissue defined by one or more stimulation parameter values.

20 Claims, 14 Drawing Sheets

(56) References Cited

U.S. PATENT DOCUMENTS

| | | | |
|---|---|---|---|
| 2006/0017749 A1* | 1/2006 | McIntyre | A61B 5/24 |
| | | | 345/664 |
| 2007/0203541 A1 | 8/2007 | Goetz et al. | |
| 2007/0288064 A1 | 12/2007 | Butson et al. | |
| 2010/0049276 A1* | 2/2010 | Blum | G06V 40/10 |
| | | | 607/45 |
| 2011/0040546 A1 | 2/2011 | Geber et al. | |
| 2011/0066407 A1 | 3/2011 | Butson et al. | |
| 2011/0093045 A1 | 4/2011 | Moffitt | |
| 2011/0191275 A1 | 8/2011 | Lujan et al. | |
| 2012/0046715 A1* | 2/2012 | Moffitt | A61N 1/36185 |
| | | | 607/59 |
| 2012/0230566 A1* | 9/2012 | Dean | A61B 5/1075 |
| | | | 382/128 |
| 2012/0265271 A1* | 10/2012 | Goetz | A61B 34/20 |
| | | | 607/59 |
| 2012/0296396 A1 | 11/2012 | Mofitt et al. | |
| 2012/0330374 A1 | 12/2012 | Blum et al. | |
| 2013/0002646 A1* | 1/2013 | Lin | G06T 7/11 |
| | | | 345/419 |
| 2013/0050208 A1* | 2/2013 | Lin | A61B 5/055 |
| | | | 345/420 |
| 2013/0116744 A1 | 5/2013 | Blum et al. | |
| 2013/0184786 A1* | 7/2013 | Goetz | G06T 17/20 |
| | | | 607/59 |
| 2013/0204327 A1 | 8/2013 | Carlton et al. | |
| 2014/0122379 A1 | 5/2014 | Moffitt et al. | |
| 2015/0088223 A1 | 3/2015 | Blum et al. | |
| 2015/0246233 A1* | 9/2015 | Kaemmerer | A61N 1/36142 |
| | | | 607/59 |
| 2017/0189700 A1 | 7/2017 | Moffitt et al. | |
| 2017/0285735 A1* | 10/2017 | Young | G06F 3/013 |
| 2017/0365103 A1* | 12/2017 | Nijlunsing | A61B 5/291 |
| 2019/0262609 A1 | 8/2019 | Brill et al. | |

OTHER PUBLICATIONS

Akram et al., "Optimal deep brain stimulation site and target connectivity for chronic cluster headache," American Academy of Neurology, published online Oct. 13, 2017, 10 pp.

Chaturvedi et al., "Patient-specific models of deep brain stimulation: Influence of field model complexity on neural activation predictions," Brain Stimulation, Jan. 8, 2010, 13 pp.

International Search Report and Written Opinion of International Application No. PCT/US2020/066628, dated Mar. 10, 2021, 16 pp.

Lobos et al., "Techniques for the generation of 3D Finite Element Meshes of human organs," Informatics in Oral Medicine: Advanced Techniques in Clinical and Diagnostic Technologies, Nov. 19, 2009, 36 pp.

Prosecution History from U.S. Appl. No. 16/733,936, now U.S. Pat. No. 11,341,717, dated Apr. 6, 2021 through Jan. 26, 2022, 79 pp.

International Preliminary Report on Patentability from International Application No. PCT/US2020/066628 dated Jul. 14, 2022, 9 pp.

* cited by examiner

GRAPHICAL DISPLAY OF VOLUME OF ACTIVATION

This application is a continuation of U.S. patent application Ser. No. 16/733,936, filed Jan. 3, 2020, the entire contents of which is incorporated herein by reference.

TECHNICAL FIELD

The disclosed technology relates to electrical stimulation and, more particularly, to graphical display rendering of volume of activation regions with respect to electrical stimulation parameters.

BACKGROUND

Electrical stimulators may be used to deliver electrical stimulation to patients to treat a variety of symptoms or conditions such as chronic pain, tremor, Parkinson's disease, epilepsy, urinary or fecal incontinence, sexual dysfunction, obesity, or gastroparesis. In general, a stimulator delivers electrical stimulation in the form of electrical pulses. A stimulator may deliver electrical stimulation via one or more leads that include electrodes located proximate to target locations associated with the brain, the spinal cord, pelvic nerves, peripheral nerves, or the stomach of a patient. Hence, stimulation may be used in different applications, such as deep brain stimulation (DBS), spinal cord stimulation (SCS), pelvic stimulation, gastric stimulation, peripheral nerve stimulation, muscle stimulation, etc.

In order to improve the efficacy of electrical stimulation, stimulators having leads and electrodes have grown in capability and complexity. For example, some lead sets include axial leads carrying ring electrodes disposed at different axial positions, and so-called "paddle" leads carrying planar arrays of electrodes. In general, a physician selects values for a number of programmable parameters in order to define the electrical stimulation. For example, the physician may select a combination of electrodes carried by one or more leads, assign polarities to the selected electrodes, select amplitudes for current, voltage, etc., pulse widths, pulse rates, etc. In addition, modern stimulators tend to have larger number of electrode combinations, larger parameter ranges, and the ability to simultaneously deliver multiple configurations by interleaving stimulation pulses. In some instances, a stimulator may deliver electrical stimulation according to multiple programs. Although these factors increase the ability of a physician to adjust for a particular patient or disease state, the burden involved in optimizing the device parameters has similarly increased.

For example, a physician may test electrode combinations by manually specifying combinations based on intuition or some idiosyncratic methodology. The physician may then record notes on the efficacy and side effects of each combination after delivery of stimulation. In some cases, efficacy can be observed immediately within the clinic. For example, spinal cord stimulation may produce paresthesia and side effects that can be observed based on patient feedback. In other cases, side effects and efficacy may not be apparent until a program has been applied for an extended period of time, as is sometimes the case in DBS. Upon receipt of patient feedback and/or observation of symptoms by the physician, the physician may then be able to compare and select from the tested stimulation programs.

In any case, electrical stimulation using leads and electrodes creates an electrical field that forms according to parameters of the stimulation designed to activate targeted tissue regions of a patient and in some instances, specific neurons or neural pathways. That is, the electrical fields produced by energized electrodes are controlled so as to target and activate various regions of a patient. Activated regions are generally referred to as volume of activation (VOA), or in more specific instances, volume of neural activation (VNA) or volume of tissue activated (VTA), etc. That is, a VOA may generally represent a VNA, VTA, stimulation field model (SFM), electrical stimulation field (ESF), or combinations thereof. In any event, such activation details may be conveyed visually to a physician, such that the physician may view, study, and understand which regions may or may not be activated by a particular stimulation program.

SUMMARY

In general, this disclosure describes devices, systems, and techniques for rendering visual representations of VOAs by manipulating vertices of a three-dimensional (3-D) mesh structure based on stimulation parameters that define an intersect between predicted activated tissue and non-activated tissue. The techniques of this disclosure may be applied using a dedicated graphics-rendering device, such as a graphics processing unit (GPU), a central processing unit (CPU), or combinations thereof. For example, processing circuitry of a GPU may identify a 3-D mesh structure, such as a 3-D mesh structure retrieved from a predefined location in graphics memory. The GPU may mutate the 3-D mesh structure to conform to an estimated VOA by adjusting vertices of the 3-D mesh structure according to an intersection between activated tissue and non-activated tissue. In any case, the processing circuitry of the GPU may graphically render the conformed 3-D mesh structure for display as a visual representation of an estimated VOA.

In some examples, a method includes receiving, by processing circuitry, a three-dimensional mesh structure associated with a plurality of electrodes of a lead, wherein the three-dimensional mesh structure comprises a plurality of vertices corresponding to locations on the three-dimensional mesh structure. The method further includes adjusting, by the processing circuitry, one or more vertices of the plurality of vertices to generate an adjusted shape of the three-dimensional mesh structure according to an intersection between activated tissue and non-activated tissue. The method further includes controlling, by the processing circuitry, a display interface to output a visual representation of the adjusted shape of the three-dimensional mesh structure.

In some examples, a computing device includes processing circuitry that receive a three-dimensional mesh structure associated with a plurality of electrodes of a lead, wherein the three-dimensional mesh structure comprises a plurality of vertices corresponding to locations on the three-dimensional mesh structure. Additionally, the processing circuitry may adjust one or more vertices of the plurality of vertices to generate an adjusted shape of the three-dimensional mesh structure according to an intersection between activated tissue and non-activated tissue. Additionally, processing circuitry may control a display interface to output a visual representation of the adjusted shape of the three-dimensional mesh structure.

In some examples, a computer-readable medium includes instructions that cause a processor to receive a three-dimensional mesh structure associated with a plurality of electrodes of a lead, wherein the three-dimensional mesh structure comprises a plurality of vertices corresponding to locations on the three-dimensional mesh structure. Additionally, the computer-readable medium including instructions to cause a processor to adjust one or more vertices of the plurality of vertices to generate an adjusted shape of the three-dimensional mesh structure according to an intersection between activated tissue and non-activated tissue. Additionally, the computer-readable medium including instructions to cause a processor to control a display interface to output a visual representation of the adjusted shape of the three-dimensional mesh structure.

In some examples, the disclosure provides a computing device for rendering a volume of activation (VOA), the computing device comprising one or more processors configured to provide means for receiving a three-dimensional mesh structure associated with a plurality of electrodes of a lead, wherein the three-dimensional mesh structure comprises a plurality of vertices corresponding to locations on the three-dimensional mesh structure, means for adjusting one or more vertices of the plurality of vertices to generate an adjusted shape of the three-dimensional mesh structure according to an intersection between activated tissue and non-activated tissue defined by tissue activation data, or stimulation parameter values, and/or electrical field data, and means for controlling a user interface to output a visual representation of the adjusted shape of the three-dimensional mesh structure.

The details of one or more examples of the disclosed technology are set forth in the accompanying drawings and the description below. Other features, objects, and advantages of the disclosed technology will be apparent from the description and drawings, and from the claims.

DETAILED DESCRIPTION

Figure 1:
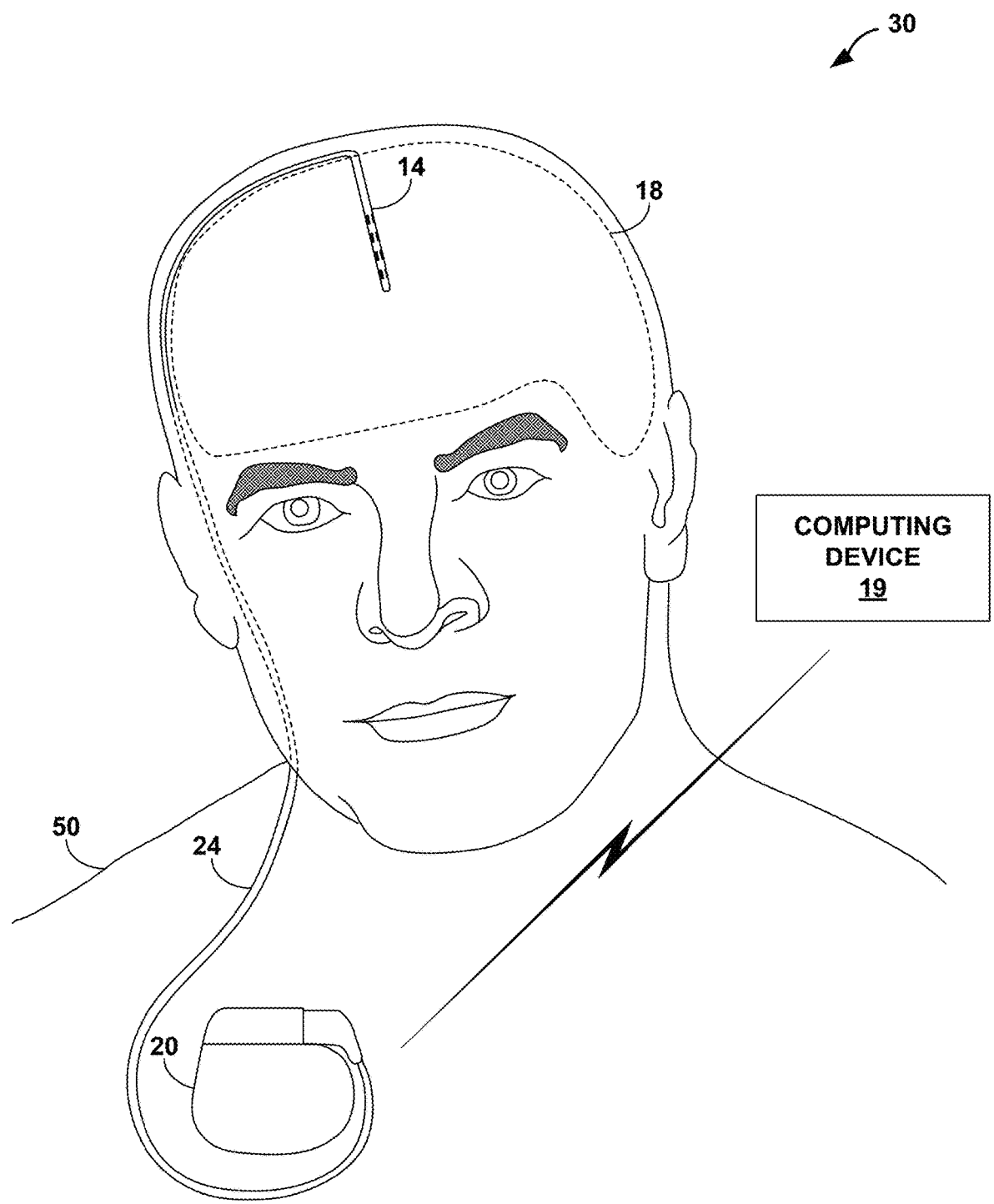
FIG. 1 is a conceptual diagram illustrating an example stimulation system that may interface with a computing device.

This disclosure is directed to devices, systems, and techniques for graphically rendering a two-dimensional (2-D) or three-dimensional (3-D) representation of a VOA for display via a display interface. For example, a CPU or a dedicated graphics-rendering device, such as a GPU, may generate a VOA visual representation by manipulating the shape of a 3-D mesh structure based on particularly defined stimulation parameters.

In some instances, rendering algorithms may be executed to render an estimated VOA for graphical display, in conjunction with or independent of the disclosed rendering algorithm. In such instances, a computing device may be configured to toggle between various rendering algorithms, for example, in response to user input. For example, a physician may request in a particular instance that a computing device render a VOA, and the computing device may use a rendering algorithm, such as marching squares, marching cubes, dividing cubes, marching tetrahedra, or other similar algorithms to render the VOA.

As one example, a computing device may determine locations between tissue fibers having a threshold of activation. The computing device may execute a marching cubes algorithm that marches lockstep through points in virtual 3-D space to determine activation regions between activated tissues and non-activated tissues. At each point, a CPU may perform a memory look-up for each of a plurality of individual triangle mesh structures that the CPU uses to assemble a final mesh structure. The CPU may then transfer the final mesh structure to a graphics-rendering device. In such examples, a computing device may be slow to render a VOA and may quickly consume battery power of a portable device, such as a tablet computer, due to the amount of processing power and memory used to execute such algorithms. In this manner, rendering a VOA using algorithms, such as marching cubes, can prove computationally expensive, inefficient, and prohibitively unworkable, especially from the perspective of the physician.

In accordance with various techniques of this disclosure, a computing device may increase efficiency with respect to rendering VOAs by leveraging a graphics-rendering device or CPU to model the VOA for display using a mutable 3-D mesh structure. As such, the techniques of this disclosure include utilizing processing circuitry, such as that of a GPU or CPU, in order to mutate a predefined mutable 3-D mesh structure to generate an adjusted shape of the 3-D mesh structure. For example, a GPU may retrieve one or more 3-D mesh structures from memory, such as cylindrical mesh structures, spherical mesh structures, partially cylindrical or spherical mesh structures, amorphous mesh structures (e.g., having a custom drawn shape), or any combinations thereof, including various other geometrical attributes.

In some examples, processing circuitry may receive estimated VOA data items and/or store the estimated VOA data items to memory. For example, processing circuitry may determine stimulation parameter data (e.g., amplitude values, polarity values, lead geometry data, etc.) and/or electrical field data values (e.g., threshold values) that define estimated VOA data items. The processing circuitry may store the estimated VOA data items to a memory device, such as to a predefined graphics memory location.

In some examples, processing circuitry of a CPU or GPU may determine electrical field threshold values based on output from an electrical field model that uses one or more stimulation parameter values as input to the model. In some instances, processing circuitry of the CPU or GPU may apply a neuron model (e.g., one that indicates one or more characteristics of patient neural tissue proximate to a lead) to the electrical field model to generate data defining an activation field model. The GPU may store one or more of the estimated VOA data items (e.g., electrical field threshold values, activation field model data, etc.) to graphics memory. In some examples, processing circuitry may store the estimated VOA data items in system memory. In such examples, processing circuitry of the CPU or GPU may effect transfer of one or more of the estimated VOA data items from system memory to graphics memory for subsequent access and utilization in graphically rendering an estimated VOA.

In addition, processing circuitry may receive data defining a particular 3-D mesh structure. For example, a CPU may receive, via a user interface, user input comprising data defining a 3-D mesh structure. The CPU may store such data to a predefined memory location, such as in system memory or graphics memory. In some examples, processing circuitry may receive one or more 3-D mesh structures as part of a software installation and/or software update, where the CPU may store the received data to a predefined memory location, such as in system memory or graphics memory. That is, processing circuitry of one or more processing units, such as a GPU, CPU, texture mapping unit (TMU), etc. may populate graphics memory or system memory with 3-D mesh structure data. In any case, processing circuitry may retrieve mesh data for one or more particular 3-D mesh structures from a predefined memory location.

In some examples, processing circuitry, such as that of CPU 88 or graphics processor 2, may identify an initial 3-D mesh structure. For example, the initial 3-D mesh structure may include a single 3-D cylindrical mesh comprising triangles that form a cylindrical shape. Processing circuitry, such as that of CPU 88 or graphics processor 2, may segment the 3-D mesh structure to determine a plurality of vertices. For example, the vertices may be determined based on intersection points of multiple 2-D slices established with respect to the 3-D mesh. Processing circuitry, such as that of CPU 88 or graphics processor 2, may then store the plurality of vertices to a location in graphics memory 8. For example, the vertices, such as vertex coordinates defined in virtual space, may be stored in texture memory 10. In such examples, when preparing to render an estimated VOA representation, processing circuitry, such as that of CPU 88 or graphics processor 2, may receive the 3-D mesh structure from graphics memory 8.

In one example, processing circuitry, such as that of CPU 88 or graphics processor 2, may receive the plurality of vertices from a predefined memory location in graphics memory 8. The plurality of vertices may define the 3-D mesh structure. The predefined memory location may be a memory location configured to store vertex coordinates and/or 3-D mesh structures (e.g., triangle data defining a single mesh structure). In some examples, processing circuitry, such as that of CPU 88, may receive the 3-D mesh structure based on user input via user interface 98. In any event, processing circuitry, such as that of CPU 88 or graphics processor 2, may receive from memory or otherwise receive the 3-D mesh structure from an external source, such that the processing circuitry may generate an adjusted shape of the 3-D mesh structure. For example, a GPU, such as graphics processor 2, may generate the adjusted shape of the 3-D mesh structure by adjusting vertices of one or more initial 3-D mesh structures or previously adjusted 3-D mesh structures, in accordance with various techniques of this disclosure.

In some instances, the 3-D mesh structure may be associated with electrodes of a lead. For example, processing circuitry may identify the initial size and shape of a particular 3-D mesh structure according to the geometry, polarity, and other parameter values relating to the lead that may also be stored in graphics or system memory. As such, the initial size and shape of the 3-D mesh structure may at least initially envelope, or surround, the energized electrodes and estimated VOA. In such examples, processing circuitry may at least initially allocate a predefined amount of virtual space between virtual elements, such as initial buffer space between an initial 3-D mesh structure and the electrical field threshold or estimated VOA, in order to perform certain digital "shrink wrap" processes described further herein.

In some examples, processing circuitry may segment the 3-D mesh structure to determine coordinates of vertices that correspond to locations on the 3-D mesh structure. For example, the GPU may establish virtual 2-D or 3-D slices through the 3-D mesh structure. In some examples, the number of slices coincides with the number of rings electrodes of a lead. In such examples, the GPU may define the vertices of the 3-D mesh structure as discrete locations upon which the virtual slices intersect a section of surface area of the 3-D mesh structure. As such, each discrete location along the segmented 3-D mesh structure may be defined as having a respective coordinate position particularly anchored in virtual 3-D space.

In some examples, the GPU may determine the initial vertex locations of an initial 3-D mesh structure based on a model of a voltage potential field defined by stimulation parameter values. The model of the voltage potential field may be generated using a field simulator, such as a Finite Element Analysis (FEA) simulator, COMSOL® simulator, etc. The voltage potential field model data may serve as electrical field data. Furthermore, the model of the voltage potential field may initially be stored in graphics memory as a 3-D voxel grid. In some examples, the GPU may slice the 3-D voxel grid of the voltage field in order to establish 2-D slices, or in some cases 3-D slices, through the voltage field. For example, the GPU may establish slices through the voxel grid at locations corresponding to contacts along a stimulation lead. The 2-D or 3-D slices may then be used to adjust vertices of an initial 3-D mesh structure along the plane of each slice. The vertices may be adjusted in accordance with one or more techniques of this disclosure to obtain a model of a VOA.

As such, the GPU may implement various graphics operations that utilize specific electrical field data and/or other stimulation parameter data (e.g., tissue activation values) to adjust vertices of the 3-D mesh structure to generate an adjusted shape of the 3-D mesh structure. For example, processing circuitry of the GPU may adjust vertex positions of the segmented 3-D mesh structure by sliding each vertex starting from a respective coordinate position of each vertex radially inward along a plane toward a surface of an estimated VOA. In some examples, the processing circuitry may slide the coordinate position inward until the adjusted vertex position aligns with data defining an electrical field threshold or in some instances, the intersection between activated tissue and non-activated tissue as defined by one or more stimulation parameter values.

In some examples, the GPU may adjust vertex positions of the segmented 3-D mesh structure and/or manipulate multiple vertex positions in parallel with one another. As such, the GPU may adjust vertices of the received 3-D mesh structure in parallel so as to shrink wrap a VOA that a CPU or GPU has estimated from electrical field and/or stimulation parameter data. In any event, the GPU may determine adjusted vertex coordinates that define an adjusted shape of the 3-D mesh structure. In this way, the GPU may generate an adjusted shape of a 3-D mesh structure that, when outputted, visually represents the estimated VOA.

In some examples, the GPU may control a display interface to output the visual representation of the estimated VOA to a display device. For example, the GPU may control a display interface to output, via a display device, a 3-D view of the adjusted shape, such as an isometric view, and/or a cross-sectional view of the adjusted shape, such as a 2-D view from a specified viewing angle or a sectioned cutaway of the adjusted shape, or any other desired VOA visual representation as defined by a user, where the VOA visual representation comprises the adjusted shape of the 3-D mesh structure or is otherwise derived from the adjusted shape of the 3-D mesh structure. In one example, the adjusted shape of the 3-D mesh structure may represent a VNA. In such examples, the VNA may correspond to electrical stimulation deliverable by a lead and according to one or more stimulation parameter values.

While some techniques of this disclosure are described with reference to particular processing circuitry (e.g., CPUs, GPUs, etc.) performing specific actions or techniques of this disclosure, the techniques of this disclosure are not so limited, and it would be understood by a person of ordinary skill in the art that the techniques of this disclosure may be applied using alternate or additional processing circuitry, such as processing circuitry of a CPU or processing circuitry of a multiple processor system, such as CPU-GPU system. In a non-limiting example, processing circuitry in a CPU-GPU system may receive data coordinates defining one or more 3-D mesh structures. The CPU may receive 3-D mesh structure data coordinates based on user input, such as from a user defining various 3-D mesh structures via a user interface.

In some examples, the CPU may automatically generate and store data coordinates defining various 3-D mesh structures, such as by independent generation, by implementing machine learning models, such as a supervised learning algorithm, and/or based on user input. The CPU may cause data corresponding to the 3-D mesh structures to be stored in memory, such as in a predefined graphics memory location or in some instances, in system memory. In addition, the CPU may store other data, such as stimulation parameter data, electrode and lead geometries, etc., in system memory or to a predefined graphics memory location, such as to texture memory. In some instances, the term "processing circuitry" as used herein may refer to joint processing circuitry of a CPU-GPU system. In some instances, however, various processing units may have dedicated processing circuitry that may comprise separate processing units.

The disclosure may provide one or more advantages. For example, the rendering of an activation volume may be done more quickly and efficiently on a GPU adjusting vertices of a three-dimensional mesh structure, as opposed to rendering an activation volume on a CPU via an algorithm, like marching cubes, dividing cubes, marching tetrahedrons, etc. A user may then more readily view side views, cross-sectional views, full 3-D views, etc. of a VOA on a user interface. In this manner, the user interface may be able to illustrate the VOAs, even in examples including leads having complex electrode array geometries, in an efficient manner that strategically allocates resources across various processing units and memory units. In addition, the starting mesh may look cleaner and/or have smoother shading, compared to other algorithms, due to the reuse of a single 3-D mesh structure.

FIG. 1 is a conceptual diagram illustrating an example system with a stimulation lead implanted in the brain 18 of a patient 50. As shown in FIG. 1, system 30 includes an implantable medical device (IMD) 20, lead wire 24 and lead 14 implanted within patient 50. In this example, lead 14 enters through the cranium of patient 50 and is implanted within brain 18 to deliver DBS. One or more electrodes of lead 14 provide electrical pulses to surrounding anatomical regions of brain 18. In some examples, more than one lead 14 may be implanted within brain 18 of patient 50 to stimulate multiple anatomical regions of brain 18 (e.g., leads placed in respective hemispheres of patient 50).

In some examples, a computing device 19 (hereinafter, "device 19") may be provided in the form of a handheld device, portable computer, or workstation that provides a UI to a physician or patient. The physician or patient interacts with the user interface to program stimulation parameters for IMD 20, or a neurostimulator, via device 19. In some examples, device 19 may be an external programmer for programming and controlling IMD 20, e.g., a medical device that can function as an electrical stimulator. Although an IMD will be described herein, device 19 may interface with external medical devices in other examples.

In addition, although application of IMD 20 to DBS is depicted in FIG. 1, electrical stimulators incorporating one or more leads may be used to deliver electrical stimulation to patients to treat a variety of symptoms or conditions (e.g., chronic pain, tremor, Huntington's Disease, Parkinson's disease, epilepsy, urinary or fecal incontinence, sexual dysfunction, obesity, gastroparesis, movement disorders, etc.). For example, stimulation may be delivered via electrode array geometries to serve different therapeutic applications (e.g., deep brain stimulation (DBS), spinal cord stimulation (SCS), pelvic stimulation, gastric stimulation, peripheral nerve stimulation, muscle stimulation, etc.). DBS via one or two leads will be described for purposes of illustration throughout this disclosure, but should not be considered limiting of the disclosed technology, as described herein.

For example, DBS may be used to treat dysfunctional neuronal activity in the brain which manifests as diseases or disorders. The exact mechanisms explaining why electrical stimulation is capable of treating such conditions of the brain are not fully known, but symptoms of these diseases can be lessened or eliminated with electrical stimulation. Certain anatomical regions of brain 18 are responsible for producing the symptoms of certain brain disorders. For example, stimulating an anatomical region called the Substantia Nigra in brain 18 may reduce the number and magnitude of tremors experienced by patient 50. Other examples include stimulation of the subthalamic nucleus, globus pallidus interna, ventral intermediate nucleus, or zona inserta. Anatomical regions such as these are targeted by a physician during implantation of lead 14 and programming of IMD 20. During implantation, the physician attempts to position the lead as close to these regions as possible.

Typical DBS leads include one or more ring electrodes placed along the longitudinal axis of the lead, such as lead 14. Each ring electrode extends around the entire circumference of the lead. Therefore, electrical current from the ring electrodes propagates radially in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects. Implanting a lead with a more complex electrode array geometry may help to customize the stimulation field. For example, stimulation fields may be delivered on a more directional basis to more selectively target specific anatomical structures. By selecting electrodes at particular angular positions, a field may be generally limited to one side of a lead rather than all sides of the lead.

Lead 14 has a particular electrode array geometry. In the example of FIG. 1, lead 14 includes four electrode "levels," i.e., at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 14. Hence, lead 14 includes multiple electrical conductors that extend from the proximal end of lead 14 to respective electrodes.

System 30 may also include multiple leads 14 or electrodes on leads of other shapes and sizes. UI 98 may allow the physician to program each lead simultaneously or require the physician to program each lead separately. While lead 14 is described for use in DBS applications throughout this disclosure as an example, lead 14, or other leads, may be implanted at any other location within patient 50. For example, lead 14 may be implanted near the spinal cord, pudendal nerve, sacral nerve, or any other nervous or muscle tissue that may be stimulated. In some examples, UI 98 may be used to program stimulation parameters of any type of electrical stimulation (e.g., SCS, pelvic nerve stimulation, etc.).

Each electrode is positioned at a different angular position around the circumference of lead 14, which has a generally circular cross-section in the example of FIG. 1. Each electrode is independently selectable so that stimulation energy can be delivered from the lead at different axial and angular positions. In some examples, lead 14 may include combinations of complex and simple electrode array geometries. Selective activation of the electrodes carried by lead 14 can produce customizable stimulation fields that may be directed to a particular side of lead 14 in order to isolate the stimulation field around a target anatomical region of brain 18.

A complex electrode array geometry generally refers to an arrangement of stimulation electrodes at multiple non-planar or non-coaxial positions, in contrast to simple electrode array geometries in which electrodes may share a common plane or axis. An example of a complex electrode array geometry may include an array of electrodes positioned at different axial positions along the length of a lead, as well as at different angular positions about the circumference of the lead. In some examples, the electrodes may appear similar to non-contiguous, arc-like segments of a ring electrode. A lead with a complex electrode array geometry may include multiple rings of electrode segments. Ring electrodes may be disposed at different axial positions. In one example, lead 14 may include, starting at the distal end of lead 14 and moving proximally along the axial length of the lead, a ring electrode, three electrodes at a first axial position and different circumferential positions, three electrodes at a second axial position and different circumferential positions, and another ring electrode. Electrode segments within a given ring may be disposed at different angular positions. In some examples, an initial electrode combination may include a ring formed by all electrodes in a given level and all electrodes in another level. For example, all electrodes at different angular positions in one axial electrode level may be selected as "+" electrodes and all electrodes at different angular positions in a different axial electrode level may be selected as "−" electrodes. In some examples, unipolar electrode rings may be selected. In addition, the lead may be cylindrical or have a circular cross-section of varying diameter.

An example of a complex electrode array geometry is an array of electrodes positioned on multiple planes or faces of a lead. As an illustration, arrays of electrodes may be positioned on opposite planes of a paddle lead or multiple faces of a lead having a polygonal cross-section in a plane transverse to the longitudinal axis of the lead. As further examples, electrodes may be arranged at different axial and angular positions on leads defining spherical, hemispherical or generally rounded surfaces. In some examples, leads may have a defined shape or be at least partially conformable to an anatomical structure.

An example of a simple electrode array geometry is an array of ring electrodes distributed at different axial positions along the length of a lead, whereas an example of a complex electrode array geometry is an array of electrodes positioned at different axial positions along the length of a lead, as well as at different angular positions about the circumference of the lead.

Producing directional or irregular stimulation fields with lead 14 allows system 30 to effectively treat certain anatomical regions of brain 18. The center of the stimulation field may be moved away from lead 14 to avoid unwanted stimulation or compensate for inaccurately placed leads. Since leads may also migrate within brain 18 or other stimulation sites slightly, a customizable stimulation field may provide a longer duration of effective electrical stimulation as stimulation needs of patient 50 change.

Programming delivery of stimulation via lead 14 is can be an involved and complex operation and may be difficult for the physician if the physician is required to systematically select each electrode of lead 14 in order to find the electrode combinations that provide minimal side effects. While the physician may still desire the ability to manually select certain general areas of electrodes, programming time may be reduced if the physician is able to view the lead and estimated VOA from different positions and manipulate axial and rotational or translational controls in an electrode view or field view. In addition, the physician may be able to manipulate or even initially define a stimulation field in a field view such that the device 19 automatically generates the stimulation parameters that would produce the stimulation field in patient 50. In such examples, device 19 may generate a visual rendering of a VOA in accordance with one or more techniques of this disclosure. In some examples, a user may manipulate the VOA visual representation, such that a user may rotate the lead and hence the estimated VOA via UI 98.

In such examples, graphics processor 2 may determine data defining an estimated VOA based on the adjusted shape of the 3-D mesh structure. In such examples, the adjusted shape may be defined by 3-D mesh data that device 19 can use to rotate, stretch, etc. the adjusted shape, such that graphics processor 2 may reuse the adjusted shape to show different perspectives of the estimated VOA without regenerating a new mesh each time a user attempt to rotate or stretch the VOA shape. In addition, device 19 may render a visual representation of the leads and electrodes in a similar manner using parameters of the lead and electrode combination. In other instances, a marching cubes algorithm may be used to render the lead and electrode combination due to the static nature of such objects, whereas the estimated VOA may be rendered using the single 3-D mesh structure, such as a single cylindrical mesh structure, as disclosed herein.

Figure 2:
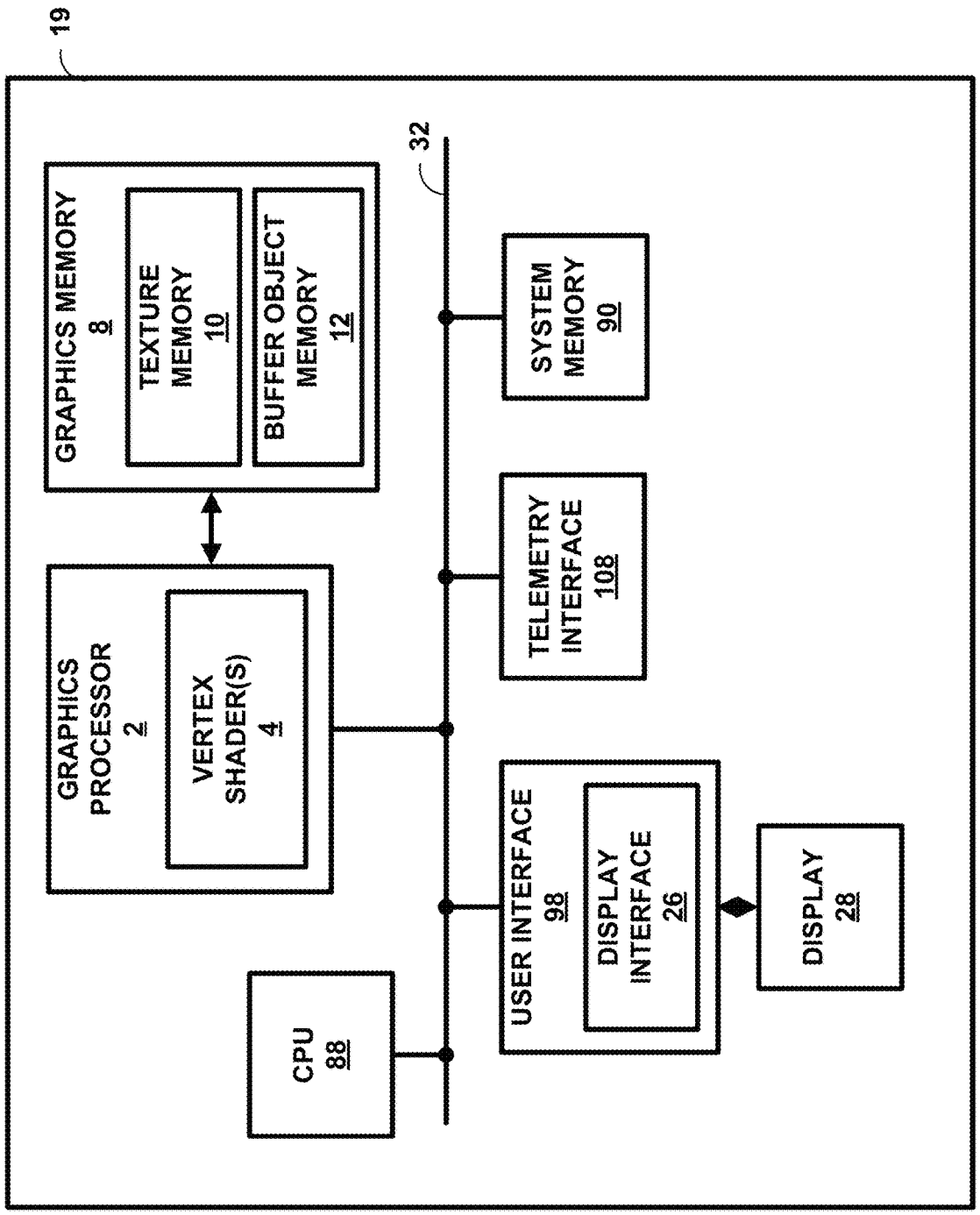
FIG. 2 is a block diagram of the example computing device of FIG. 1 configured to perform one or more of the example techniques described in this disclosure.

FIG. 2 is a block diagram of device 19 configured to perform one or more of the example techniques described in this disclosure. In the example of FIG. 2, device 19 includes CPU 88, system memory 90, graphics processor 2, graphics memory 8, telemetry interface 108, and user interface (UI) 98.

In some examples, a user (e.g., physician, clinician, patient, etc.) may interact with device 19 to program and control IMD 20. In some examples, device 19 may include a remote server, such as a cloud server, configured to perform data analytics and/or data storage. In another example, device 19 may be provided in the form of a handheld device, portable computer, or workstation. For example, device 19 may be a computer tablet programmer that a physician or patient interacts with via UI 98 to program stimulation parameters for IMD 20. Hence, various aspects of UI 98 described herein may be provided in the form of a physician programmer, a patient programmer, or both. A physician programmer may employ most or all programming functionality, such as adjustment to most or all parameters, generation of stimulation of programs, viewing diagnostic information, and the like. A patient programmer may have a different interface and have limited functionality as compared to the physician programmer, such as adjustment limited to only some parameters that define stimulation, selection of pre-determined programs, and/or turning stimulation on and off.

In examples where device 19 comprises a remote data server, such as a cloud server, device 19 may receive stimulation parameter data from another computing device or medical device, render a graphical depiction of the estimated VOA on device 19, or in some instances, generate data for an adjusted shape of a 3-D mesh structure representing the estimated VOA, and transmit the adjusted shape data to another computing device, such as a programmer. The graphics-rendering device of the other computing device (e.g., the programmer) may then render the adjusted shape of the 3-D mesh structure for display.

In another example, device 19 may include a programmer that transmits stimulation parameter data or electrical field data to a remote server, where the remote server may generate data for an adjusted shape of a 3-D mesh structure and transmit the data back to device 19, where device 19 may render a visual representation of the adjusted shape via display interface 26.

CPU 88 may comprise processing circuitry, such as a general-purpose or a special-purpose processor that controls operation of device 19. A user may provide input to device 19 that commands CPU 88 to execute one or more software applications. The software applications that execute on CPU 88 may include, for example, a graphical user interface (GUI) application, a graphics editing application, or another program. For example, CPU 88 may execute a software application that allows a physician to select electrode configurations or stimulation programs and further visualize VOAs corresponding to particular stimulation programs or electrode configurations. In some examples, CPU 88 may include a microprocessor, a microcontroller, a DSP, an ASIC, an FPGA, or other equivalent discrete or integrated logic circuitry. In some examples, CPU 88 may be configured to perform the techniques of this disclosure, such that CPU 88 manipulates the vertices of the mesh structure. In such examples, CPU 88 may communicate information regarding the adjusted shape of the mesh structure, such as the adjusted positions of vertices, to graphics processor 2. As described below, graphics processor 2 may store the adjusted shape data to graphics memory 8. Graphics processor 2 or CPU 88 may then control display interface 26 to output a visual representation of the adjusted shape of the 3-D mesh structure to display 28.

In some examples, one software application may include SureTune® developed by Medtronic, Inc., of Minneapolis, MN. SureTune® is a therapy planning platform used to model VOAs around individual contacts. In addition, the platform can apply neuron models coupled to finite-element simulations to generate VOAs. In some examples, the techniques of this disclosure may run on a SureTune® platform or similar platform thereto. In such examples, the 3-D mesh structures, such as a cylindrical triangle mesh structure, may be loaded on CPU 88, rather than graphics processor 2. In addition, a user may be able to toggle between various rendering approaches using the software application, such as by toggling between a cylindrical mesh adjustment technique and a marching cubes technique.

System memory 90 may include any volatile, non-volatile, magnetic, optical, or electrical media, such as a random-access memory (RAM), static RAM (SRAM), dynamic RAM (DRAM), non-volatile RAM (NVRAM), read-only memory (ROM), programmable read only memory (PROM), erasable PROM (EPROM), electrically-erasable programmable ROM (EEPROM), flash memory, magnetic data media, optical storage media, or any other digital media. System memory 90 may store programs specifying electrode combinations, electrode polarities, and stimulation parameters for download to the IMD 20. In some examples, system memory 90 may store an evaluation sequence that guides the user in selection of electrode combinations and stimulation parameters, or automatically selects electrode combinations and stimulation parameters for evaluation of efficacy. In some examples, system memory 90 may include efficacy information for particular programs. In addition, system memory 90 may include a driver that CPU 88 may execute to control operation of graphics processor 2.

Graphics processor 2 may include a GPU or other dedicated graphics-rendering device. Graphics processor 2 may include various components, such as vertex shaders 4. In some examples, graphics processor 2 may include other components, such as geometry shaders, fragment shaders, pixel processors, etc. In any event, graphics processor 2 may implement graphics primitive operations and in addition, may include programmable shading. In some examples, a vertex shader program may execute on vertex shader(s) 4. In some instances, shader programs may implement looping or lengthy floating-point mathematical operations that allow for various image-array operations.

Vertex shader(s) 4 generally operate on vertices in 2-D or 3-D space. In some examples, vertex shader(s) 4 may perform oversampling and interpolation techniques when adjusting or defining vertex positions. In some examples, vertex shader(s) 4 may operate in an Open Graphics Library (OpenGL®) application program interface (API). In some examples, shader programs can run entirely on CPU 88. In addition to an OpenGL®, vertex shader(s) 4 can operate in other graphics frameworks, such as Direct3D®, QuickDraw® 3D, an Open Graphics Library Embedded Systems (OpenGL ES) API, a WebGL API, a RenderMan API, an X3D API, Vulkan™, Metal, or any other public or proprietary standard graphics API. In some examples, in order to process graphics rendering instructions, CPU 88 may issue one or more graphics rendering commands to graphics processor 2 (e.g., through a GPU driver) to cause graphics processor 2 to perform some or all of the rendering of the graphics data. In some examples, the graphics data to be rendered may include a list of graphics primitives, e.g., points, lines, triangles, quadrilaterals, triangle strips, etc. For example, graphics processor 2 may render a cylindrical 3-D mesh structure comprising triangles.

Examples of graphics memory 8 include one or more volatile or non-volatile memories or storage devices, such as RAM, SRAM, DRAM, NVRAM, ROM, EPROM, EEPROM, flash memory, a magnetic data media, an optical storage media, or any other digital media. Graphics memory 8 may be a local memory storage device for graphics processor 2. Graphics memory 8 may include texture memory 10, buffer object memory 12, etc. In some examples, buffer object memory 12 may include texture buffers, vertex buffers, etc. In addition, texture memory 10 may store stimulation parameter values and/or electrical field data values. Texture memory 10 may also store data for one or more mutable 3-D mesh structures. In some examples, the 3-D mesh structures may comprise a set of connected primitive polygons, such as triangle meshes, that have edges or vertices defined by 3-D positions in 3-D space. For example, a set of connected triangles may provide a model of a 3-D object, such as a single 3-D cylindrical mesh structure. As such, processing circuitry may mutate the 3-D object to fit an estimated VOA according to an intersection between activated tissue and non-activated tissue defined by one or more stimulation parameter values.

In some examples, one or more 3-D mesh structures may be loaded from CPU 88 to graphics processor 2. Graphics processor 2 may store the one or more mesh structure to graphics memory 8. In some examples, graphics processor 2 or CPU 88 may pre-allocate an amount of memory for the one or more mesh structures in graphics memory 8. The amount of memory that is allocated is dependent on the resolution of the initial 3-D mesh structure. For example, graphics processor 2 or CPU 88 may define an initial 3-D mesh structure (e.g., a mesh cylindrical structure) as having a particular number of adjustable vertices. In one example, graphics processor 2 or CPU 88 may predefine a particular 3-D mesh structure as having 5,000 vertices. In such examples, graphics processor 2 or CPU 88 may pre-allocate a buffer in graphics memory 8 to store data defining the 3-D mesh structure. In an illustrative example involving 5,000 vertices, graphics processor 2 or CPU 88 may determine the size of the buffer based on the number of coordinates defining each vertex and the amount of memory space used to store each coordinate. For example, each vertex may be defined by a particular coordinate system (e.g., three-coordinate or xyz-coordinate system). In addition, each coordinate may use X number of bytes. As such, graphics processor 2 or CPU 88 may pre-allocate a buffer to store the 3-D mesh structure data that has a size equal to X times the number of coordinates times the number of vertices comprising the 3-D mesh structure. In a non-limiting and illustrative example, graphics processor 2 or CPU 88 may pre-allocate a 60,000 byte buffer in graphics memory 8 to store the data defining a 3-D mesh structure having 5,000 vertices, where the memory utilizes four bytes per coordinate and each vertex utilizes three coordinates.

In some examples, CPU 88 may instruct graphics processor 2 to use one 3-D mesh structure or a combination of 3-D mesh structures stored in graphics memory 8 to graphically render a VOA. In some examples, the initial shape of the mesh structure may be defined based on the respective polarities of energized electrodes, such that graphics processor 2 loads from graphics memory 8 a shape that conforms to an initial VOA shape estimation.

Display 28 may include a monitor, a television, a projection device, a liquid crystal display (LCD), a plasma display panel, a light emitting diode (LED) array, an organic LED (OLED), a cathode ray tube (CRT) display, electronic paper, a surface-conduction electron-emitted display (SED), a laser television display, a nanocrystal display or another type of display unit. Display 28 may be integrated within device 19. For instance, display 28 may be a screen of a mobile telephone handset, a tablet computer, a programmer, or a laptop. Alternatively, display 28 may be a stand-alone device coupled to device 19 via a wired or wireless communications link. For instance, display 28 may be a computer monitor or flat panel display connected to a personal computer via a cable or wireless link. In some examples, display 28 may be a touchscreen display that incorporates presence sensitive elements configured to detect the presence and/or touching of the finger(s) of a user.

Display interface 26 may retrieve data from system memory 90 or graphics memory 8 and configure display 28 to display an image represented by generated image data, such as the adjusted 3-D mesh structure. In some examples, display interface 26 may include a digital-to-analog converter (DAC) that is configured to convert the digital values retrieved from system memory 90 or graphics memory 8 into an analog signal consumable by display 28. In some examples, display interface 26 may pass the digital values directly to display 28 for processing. In any event, processing circuitry, such as that of CPU 88 and/or graphics processor 2, may control display interface 26 to output a visual representation of the adjusted of the 3-D mesh structure to display 28.

A user may interact with CPU 88 via UI 98 in order to identify efficacious electrode combinations and stimulation parameters. In some examples, UI 98 may include display interface 26, as shown in FIG. 2. In any event, UI 98 may include an interface able to receive user input and output for display a rendering of an adjusted 3-D mesh structure. UI 98 may include a touch screen interface. For example, display interface 26 may include a touch screen interface able to receive touch input configured to detect the presence and/or touching of the finger(s) of a user.

In some examples, certain input media of UI 98 may include a rotational controller and/or an axial controller. For example, an axial controller permits a user to move electrode combinations or stimulation fields up or down along the length of a lead by selecting different combinations of electrodes, whereas the rotational controller permits the user to move electrode combinations or stimulation fields around the lead by selecting combinations of electrodes at different angular positions. In some examples, a user may interact with UI 98 including rotational controllers and/or axial controllers as described in U.S. application Ser. No. 11/591,188 by Goetz et al., entitled "PROGRAMMING INTERFACE WITH A CROSS-SECTIONAL VIEW OF STIMULATION LEAD WITH COMPLEX ELECTRODE ARRAY GEOMETRY," filed on Oct. 31, 2006, incorporated herein by reference in its entirety. In addition, CPU 88 may use an evaluation sequence to run a user-controlled test of a sequence of electrode combinations to identify effective electrode combinations. CPU 88 may receive a set of electrode combinations to test and store the set of electrode combinations as a set of programs. In some examples, CPU 88 may execute an electrode combination search algorithm according to an evaluation sequence stored in memory 90. In any case, the techniques of this disclosure may be used to graphically render an estimated VOA using stimulation parameter values as defined by various tests, programs, or evaluation sequences.

In some examples, CPU 88 may control IMD 20 via telemetry interface 108, which may include circuitry configured to transmit information to another device. In particular, CPU 88 may transmit programming signals to IMD 20 via telemetry interface 108. As a sequence of electrode combinations proceeds, the programming signals may be transmitted at a rate consistent with the control input provided by a user. In this manner, the user may quickly observe the effects of each increment in the change between electrode combinations. That is, processing circuitry, such as that of graphics processor 2 may graphically render a visual representation of VOAs estimated upon each incremental change. Graphics processor 2 may periodically render an adjusted shape of the 3-D mesh structure, such as a cylindrical mesh structure. In some examples, graphics processor 2 may determine changes in the VOA shape relative to a previously adjusted shape, such as by adjusting previously adjusted vertices or in some instances, graphics processor 2 may determine changes using the original 3-D mesh structure. In another examples graphics processor 2 may use a different 3-D shape and/or size depending on the stimulation parameters as the stimulation parameters change.

In some examples where the physician defines the desired stimulation field or modifies a stimulation field from UI 98, device 19 may automatically generate the stimulation parameter values required by the stimulation generator to generate the desired stimulation field. Device 19 may then store the parameter values to memory, such as to texture memory 10 or another location in graphics memory 8. Processing circuitry, such as that of graphics processor 2 or CPU 88, may use such parameter values to determine an intersection between activated tissue and non-activated tissue and adjust vertices of the 3-D mesh structure according to the intersection. In addition, device 19 may transmit the parameter values to IMD 20 via telemetry interface 108.

In addition, CPU 88 may transmit stimulation parameter data to an external data server via telemetry interface 108. For example, CPU 88 may transmit stimulation parameter data to a cloud server configured to determine data coordinates for an estimated VOA in accordance with one or more techniques of this disclosure. As such, the external data server may transmit the estimated VOA data coordinates to CPU 88 for storage and/or subsequent display rendering. For example, processing circuitry of device 19 may receive the estimated VOA data coordinates from an external server, generate an adjusted shape of a 3-D mesh structure, and render the adjusted shape for display in accordance with one or more techniques of this disclosure. In some instances, device 19 may interface with other devices via network technology similar to that provided by the Medtronic CareLink® Network developed by Medtronic, Inc., of Minneapolis, MN.

The techniques described herein may be used during test or evaluation modes to assist a physician in visualizing VOAs displayed by various user interfaces, while the physician selects different electrode segment combinations. For example, the visualized VOAs may be presented with respect to electrodes of one or more leads and/or a representation of patient anatomy so that the physician can identify which anatomical structures will be activated by the chosen parameter values. As such, the techniques of this disclosure may be implemented in a programmer (e.g., physician programmer, patient programmer, external programmer, etc.). As described below, the rendering techniques of this disclosure are not necessarily limited to use with particular types of stimulators, and may be used in conjunction with other stimulators (e.g., external stimulators) that deliver stimulation, for example, via percutaneous leads.

The various structures illustrated in FIG. 2 may be configured to communicate with each other using a bus 32. Bus 32 may be any of a variety of bus structures, such as a third-generation bus (e.g., a HyperTransport bus or an InfiniBand bus), a second-generation bus (e.g., an Advanced Graphics Port bus, a Peripheral Component Interconnect (PCI) Express bus, or an Advanced eXtensible Interface (AXI) bus) or another type of bus or device interconnect. It should be noted that the specific configuration of buses and communication interfaces between the different components shown in FIG. 2 is merely exemplary, and other configurations of devices and/or processing unit(s) with the same or different components may be used to implement the techniques of this disclosure.

Figure 3:
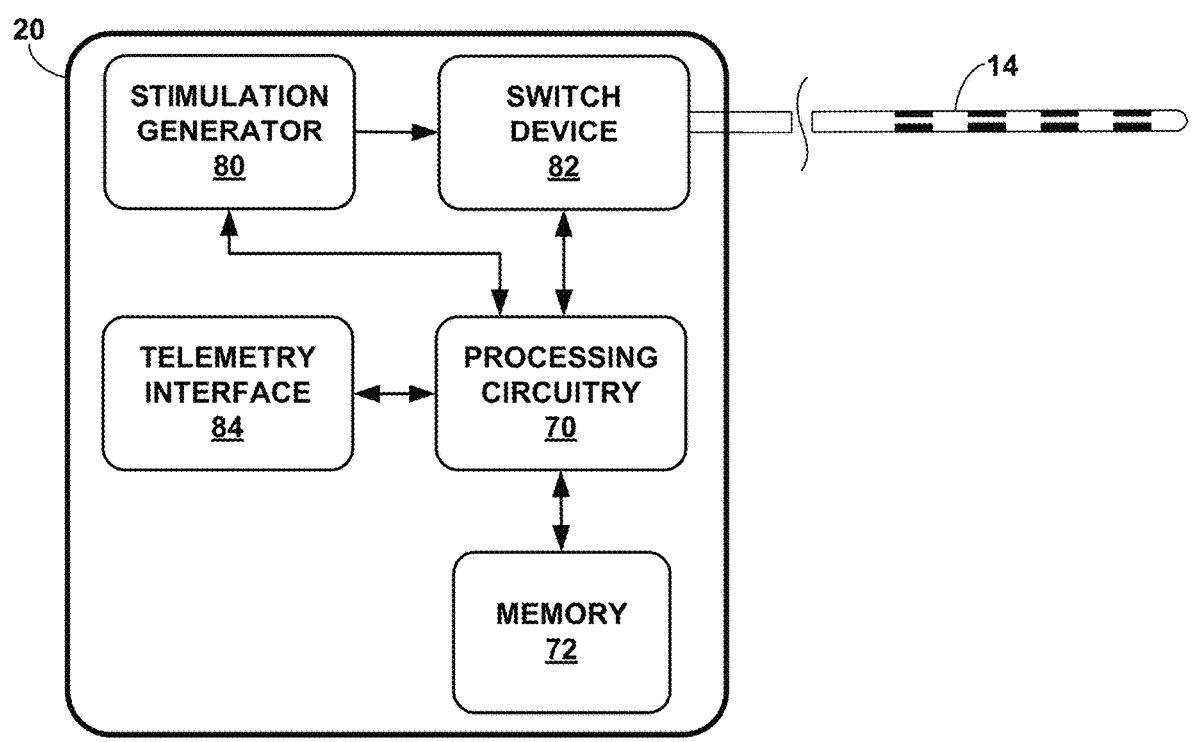
FIG. 3 is a block diagram illustrating an example stimulator for delivery of electrical stimulation via one or more leads.

FIG. 3 is a block diagram illustrating an example IMD 20 for delivery of electrical stimulation via one or more leads. As shown in the example of FIG. 3, the IMD 20 includes lead 14 (of FIG. 1), processing circuitry 70, memory 72, stimulation generator 80, switch device 82, and telemetry interface 84. IMD 20 delivers electrical stimulation via electrodes carried by one or more leads 14. In the example illustrated in FIG. 3, lead 14 includes four electrode levels, each of which may include multiple non-contiguous electrodes at different angular positions about the circumference of lead 14. In some examples, IMD 20 may include a plurality of leads 14 that each has one or more electrodes. In some examples, processing circuitry 70 controls a switch device 82 to apply pulses generated by stimulation generator 80 to various electrodes. Although not shown, switch device 82 may also connect electrodes of lead 14 to sensing circuitry within IMD 20 that is configured to sense electrical signals from the patient, as controlled by processing circuitry 70.

Memory 72 includes computer-readable instructions that, when executed by processing circuitry 70, cause IMD 20 to perform various functions. Memory 72 may include any volatile, non-volatile, magnetic, optical, or electrical media, such as a RAM, ROM, NVRAM, EEPROM, flash memory, or any other digital media. Memory 72 may include programs, program groups, and/or operating instructions. Each program defines a particular stimulation program in terms of electrode combination, electrode polarity, current or voltage amplitude, pulse width and pulse rate. A program group defines a group of programs that may be delivered together on an overlapping or non-overlapping basis. Operating instructions guide general operation of IMD 20 under control of processing circuitry 70.

Stimulation generator 80 produces stimulation signals (e.g., pulses and/or continuous waves) for delivery to the patient via one or more electrodes. In some examples, stimulation generator 80 may produce continuous sine waves or other non-pulse signals for delivery to patient 50. Processing circuitry 70 controls stimulation generator 80 according to programs and/or program groups stored in memory 72 to apply particular stimulation parameters (e.g., amplitude, pulse width, pulse rate, etc.) as specified by one or more programs. Processing circuitry 70 may include a microprocessor, a controller, a digital signal processor (DSP), an application specific integrated circuit (ASIC), a field-programmable gate array (FPGA), or equivalent discrete or integrated logic circuitry.

Stimulation generator 80 may be a single- or multi-channel stimulation generator. In some examples, stimulation generator 80 and switch device 82 may be configured to deliver multiple channels on a time-interleaved basis. In such examples, switch device 82 serves to time division multiplex the output of stimulation generator 80 across different electrode combinations. For testing of electrode combinations, processing circuitry 70 controls stimulation generator 80 to smoothly shift stimulation energy between different electrode combinations. In response, stimulation generator 80 shifts between electrode combinations of different programs by incrementally adjusting the amplitudes of the electrode combinations to smoothly shift from one electrode combination to another.

In some examples, device 19 controls IMD 20 to test electrode combinations so that a user may identify desirable combinations. Telemetry interface 84 supports wireless communication between IMD 20 and device 19 under control of processing circuitry 70. In some examples, processing circuitry 70 may receive values for stimulation parameters, such as amplitude and electrode combination, from device 19 via telemetry interface 84, and deliver one or more stimulation pulses according to the received stimulation parameters. In some examples, an electrode combination may include a subset of one or more electrodes located on one or more leads 14 coupled to IMD 20. The electrode combination also refers to the polarities of the electrode segments in the selected subset. The electrode combination, electrode polarities, amplitude, pulse width and pulse rate together define a program for delivery of electrical stimulation by IMD 20 via lead(s) 14. By selecting particular electrode combinations, a physician can target particular anatomic structures, and by selecting values for amplitude, pulse width and pulse rate, the physician can optimize electrical stimulation.

As such, device 19 may render an estimated VOA based on the above stimulation parameters and render a continuous real-time sequence of estimated VOA visual representations in accordance with one or more techniques of this disclosure. For example, device 19 may adjust the shape of a three-dimensional mesh structure in response to changes in stimulation parameter settings, such that graphics processor 2 continuously or automatically adjusts the vertices of the three-dimensional mesh structure as the stimulation parameter settings change in real-time.

Figure 4:
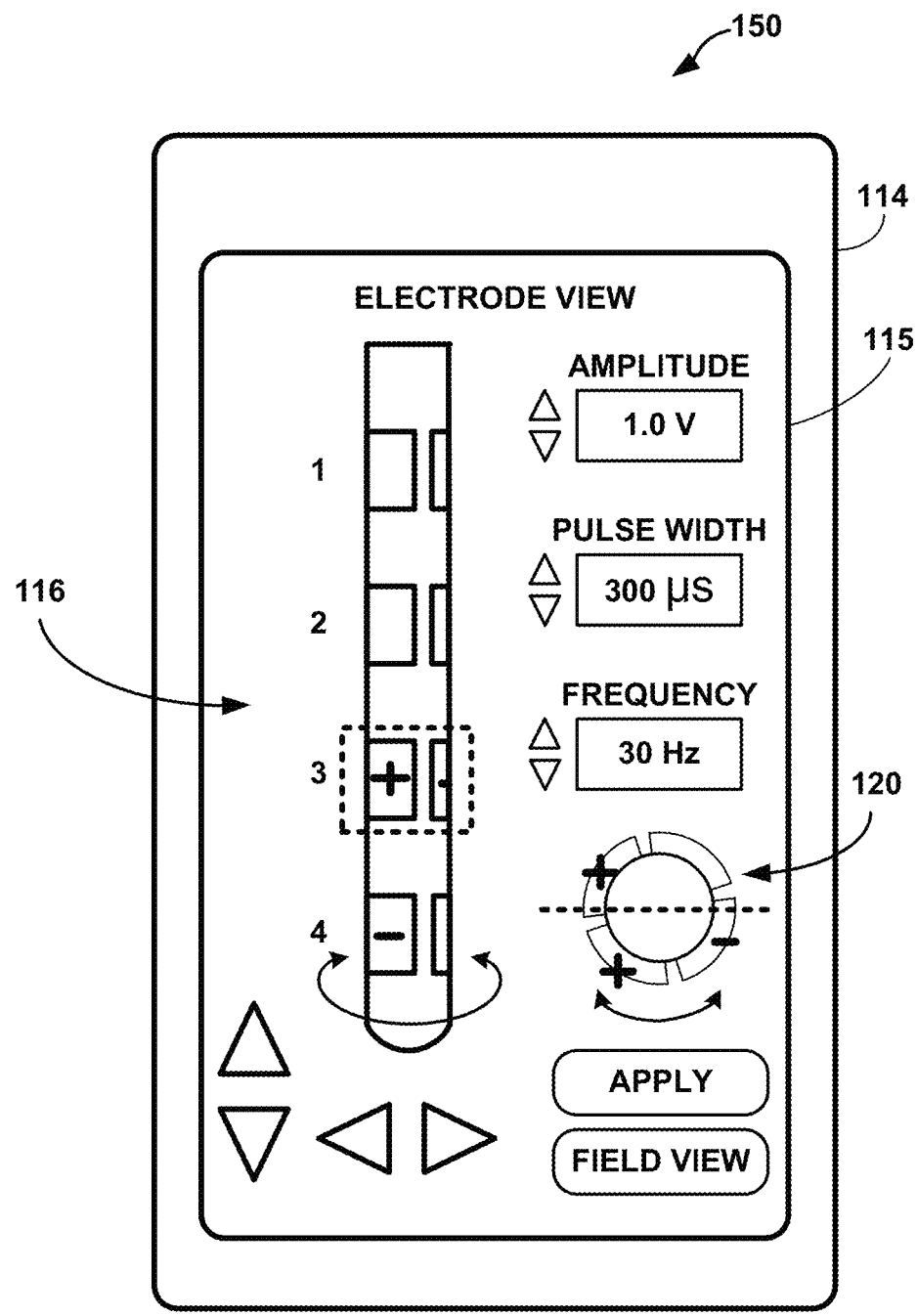
FIG. 4 is a schematic diagram illustrating an example user interface presented by the computing device of FIG. 2.

FIG. 4 is a schematic diagram illustrating an example UI that may receive input from a user regarding various electrode combinations, stimulation parameters, etc. For example, UI 150 may present an electrode view in which a user selects individual electrodes, combinations of electrodes, and stimulation parameter values, and views the electrodes using either a side view or a cross-sectional view. In the example of FIG. 4, a UI 150 is provided by a device 114, such as device 19 in some examples. UI 150 includes a display 115 that shows a single lead having four electrode levels. In some examples, display screen 115 may be a touchscreen. In this example, each electrode level includes four electrodes arranged at different angular positions around the circumference of the lead. UI 150 provides a side view 116 of the lead, and a cross-sectional view 120 of a selected level of the lead, such as a graphical representation of lead 14. In some examples, cross-sectional view 120 may include views of electrodes from all levels of lead 14 at the same time. Side view 116 shows all of the electrodes along one side of the lead. In particular, side view 116 is a 2-D view that illustrates approximately 180 degrees of the circumference of the lead, and the axial length of a distal portion of the lead.

In systems that include more than one lead 14, UI 150 may provide lead representations of two or more leads. In some examples, UI 150 may further include a "Field View" button that enables the user to activate a different viewing mode. In the field view mode, the user may manipulate a representation of a stimulation field produced by an electrode combination and a set of parameter values. Processing circuitry, such as that of CPU 88, may use data received using a UI, such as the example UI shown in FIG. 4, to determine intersection regions defined by one or more stimulation parameter values. The processing circuitry may use the stimulation parameter values received via a UI, such as the example UI shown in FIG. 4, to determine activated volume of tissue and then adjust vertices of a 3-D mesh structure to generate an adjusted shape of the 3-D mesh structure that visually represents a VOA, VNA, electrical field, stimulation field, or other stimulation region of interest. As such, processing circuitry, such as that of CPU 88, may first determine the VOA parameters (e.g., activated tissue regions, thresholds between activated tissue and non-activated tissue defined by one or more stimulation parameter values, intersections between activated tissue and non-activated tissue, etc.) before the VOA may be rendered by adjusting vertices of a 3-D mesh structure. Additional user interfaces will be described in the context of the disclosed technology, and in some examples, device 19 may provide certain UIs that resemble certain UIs described in U.S. application Ser. No. 11/591,188 by Goetz et al., entitled "PROGRAMMING INTERFACE WITH A CROSS-SECTIONAL VIEW OF STIMULATION LEAD WITH COMPLEX ELECTRODE ARRAY GEOMETRY," filed on Oct. 31, 2006, incorporated herein by reference in its entirety.

Figure 5:
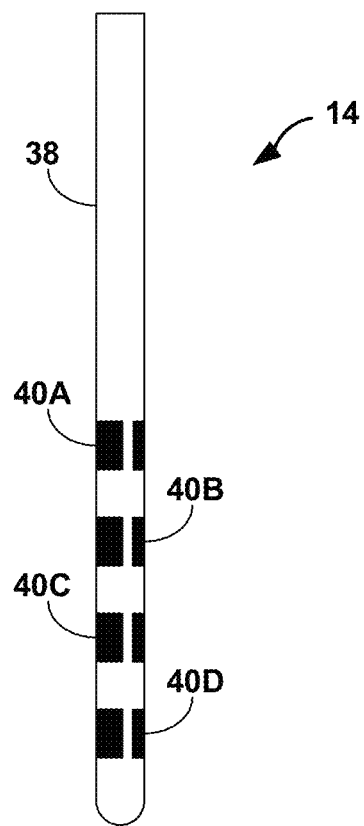
FIG. 5 is a conceptual diagram illustrating an example stimulation lead, such as the example stimulation lead of FIG. 3.

FIG. 5 is a conceptual diagram illustrating an example stimulation lead 14. As shown in FIG. 5, lead 14 includes four electrode levels 40 (40A-40D) located at various axial positions along the lengths of lead housing 38. For example, one or more of the electrode levels may be located at the distal end of lead 14. While various techniques of this disclosure are described with reference to four electrode levels for example, the techniques of this disclosure are not so limited, and a person of skill in the art will understand that any number of electrode levels may be used in keeping with the spirit of this disclosure. For example, lead 14 may include eight electrode levels, ten electrode levels, sixteen electrode levels, etc., where some or all levels include segmented electrode combinations. That is lead 14 may include a combination of segmented electrodes and ring electrodes. In a non-limiting example, lead 14 may include four electrode levels having a 1-3-3-1 configuration. In this example, the first and fourth levels of lead 14 may include single ring electrodes, whereas the middle levels may each include three segmented electrodes. Other combinations may be achieved, with the VOA rendering algorithm being configured to render VOAs produced by such combinations, in accordance with the various techniques of this disclosure. In another illustrative example, lead 14 may include a bullet tip electrode. In addition, lead 14 having a bullet tip electrode may further include a mixture of electrode rings and/or levels of segmented electrodes.

In some examples, electrode levels 40A-40D may be equally spaced along the length of lead housing 38. Each electrode may be substantially rectangular in shape. In some examples, the individual electrodes may have alternative shapes (e.g., circular, oval, triangular, etc.). In some examples, electrode levels 40 may not be evenly spaced along the longitudinal axis of the lead 14. For example, electrode levels 40C and 40D may be spaced approximately 3 millimeters (mm) apart, while electrodes 40A and 40B may be 10 mm apart.

In some examples, lead 14 may be substantially cylindrical in shape, and thus, an expected VOA shape may be defined as such. For example, the 3-D mesh may be selected as a cylindrical 3-D mesh to mirror the shape of the lead 14. In some examples, lead 14 may be substantially straight and rigid, or include one or more curves to reach target anatomical regions of brain 18. In some examples, lead 14 may be similar to a flat paddle lead or a conformable lead shaped for patient 50. In some examples, lead 14 may be any of a variety of different polygonal cross sections taken transverse to the longitudinal axis of the lead. In addition, lead 14 may have a so-called bullet-nose distal tip, blunt tip, etc. In any event, the size and shape 3-D mesh structure may be selected based on the configuration of lead 14. For example, an amorphously shaped 3-D mesh structure may be selected in cases where lead 14 has a bullet-nose distal tip.

Lead housing 38 may continue directly into lead wire 24 of FIG. 1. In some examples, lead housing 38 may include an angled connector that allows lead 14 to be inserted into brain 18. In some examples, the entire lead extending from IMD 20 to the stimulation site may have a continuous lead body. Lead 14 may continue to a proximal connector end. In some examples, the connector end may plug into an extension that continues down to IMD 20.

In some examples, lead 14 may be implanted within brain 18 at a location determined by the physician to be near an anatomical region to be stimulated. Each electrode level 40 may have one or more electrodes located at different angular positions around the circumference of lead housing 38. In one example, each electrode level 40 includes four separate electrodes at four different angular positions. Electrodes at different levels, but the same angular positions, may be aligned with one another in a direction parallel to the longitudinal axis of lead 14.

In some examples, electrodes of different electrode levels may be staggered at different angular positions around the circumference of lead housing 38. Also, in some examples, different electrode levels may include different numbers of electrodes. In addition, lead 14 may include asymmetrical electrode locations around the circumference of lead 14 or electrodes of the same level that have different sizes. These electrodes may include semi-circular electrodes that may or may not be circumferentially aligned between electrode levels. Various combinations of electrode levels having different numbers of electrodes are contemplated.

In some examples, lead housing 38 may include a radiopaque stripe (not shown) along the outside of the lead housing. The radiopaque stripe corresponds to a circumferential location that allows the physician to identify electrodes in a transverse cross-sectional view of lead 14 with respect to the orientation of the lead within tissue of patient 50. In some examples, a physician can use one or more markers (e.g., radiopaque stripes, tabs, detents, etc.) to assess the orientation of lead 14 based on images of patient 50. In such examples, the physician may note the position of markings along lead wire 24 during implantation to determine the orientation of lead 14 within patient 50. In some examples, orientation of lead 14 may be needed to program the stimulation parameters. As such, processing circuitry may use information regarding the electrodes and lead 14 configuration to determine the adjusted shape of the 3-D mesh structure. For example, graphics processor 2 may use such information to determine an initial size of the 3-D mesh structure such that the starting 3-D mesh structure at least envelopes energy electrodes at the extremities (e.g., highest and lowest point energized electrodes).

Figure 6A:
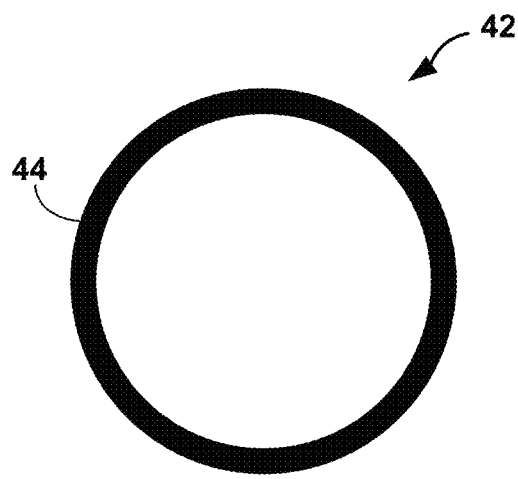
FIGS. 6A-6C are cross-sections of example stimulation leads having one or more electrodes around the circumference of the lead.
Figure 6B:
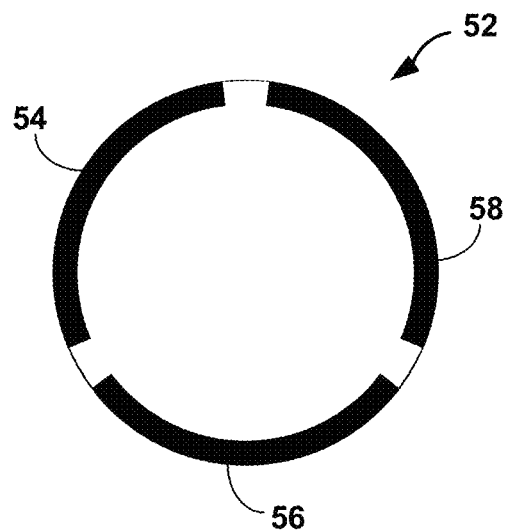
Figure 6C:
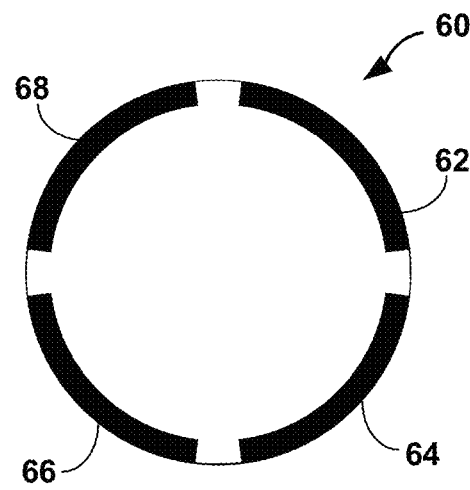

FIGS. 6A-6C are transverse cross-sections of example stimulation leads having one or more electrodes around the circumference of the lead. As shown in FIGS. 4A-4C, one electrode level, such as one of electrode levels 40 of lead 14, is shown to include one or more electrodes. FIG. 6A shows an electrode level 42 that includes circumferential electrode 44. Circumferential electrode 44 encircles the entire electrode level 42 and forms a ring electrode. Circumferential electrode 44 may be utilized as a cathode or anode as configured by the UI.

FIG. 6B shows electrode level 52 which includes three equally sized electrodes 54, 56 and 58. Each electrode 54, 56 and 58 encompasses approximately 110 degrees of the circumference of electrode level 52. In some examples, spaces of approximately 10 degrees separate electrodes 54, 56 and 58. Electrodes 54, 56 and 58 may be independently programmed as an anode or cathode for stimulation.

FIG. 6C shows electrode level 60 which includes four electrodes 62, 64, 66 and 68. Each electrode 62-68 covers approximately 80 degrees of the circumference with approximately 10 degrees of insulation space between the electrodes. In some examples, up to ten or more electrodes may be included within an electrode level. In some examples, consecutive electrode levels of lead 14 may include a variety of electrode levels 42, 52 or 60. In this manner, various stimulation field shapes may be produced within brain 18 of patient 50. In addition, circumferential electrodes may not be aligned along the length of their respective lead. Further, the above-described sizes of electrodes within an electrode level are merely examples, and the disclosed technology is not limited to rendering VOAs associated with electrodes of the example electrode sizes. Also, the insulation space, or non-electrode surface area, between adjacent electrodes may be of varying size.

In some examples, the space may be between approximately 1 degree and approximately 20 degrees. More specifically, the space may be between approximately 5 and approximately 15 degrees. Smaller spaces may allow a greater volume of tissue to be stimulated. In some examples, circumferential electrode size may be varied around the circumference of an electrode level. In addition, insulation spaces may vary in size as well. Such unsymmetrical electrode levels may be used in leads implanted at tissues needing certain shaped stimulation fields. In some examples, the stimulation parameter values may include information regarding the lead and electrode configuration, including the insulation space dimensions, etc. For example, processing circuitry, such as processing circuitry of CPU 88 or graphics processor 2, may utilize insulation space dimensions and electrode sizes to determine tissue activation data and/or stimulation parameter values, that may be used to determine activated volume of tissue and then adjust the one or more vertices of the plurality of vertices to generate the adjusted shape of the three-dimensional mesh structure or determine electrical field data of the particular lead and electrode configuration. In some examples, processing circuitry, such as processing circuitry of CPU 88 or graphics processor 2, may include electrode size, spacing, and other parameters when determining one or more voltage potential field models using a field simulator (e.g., COMSOL®, etc.).

Figure 7:
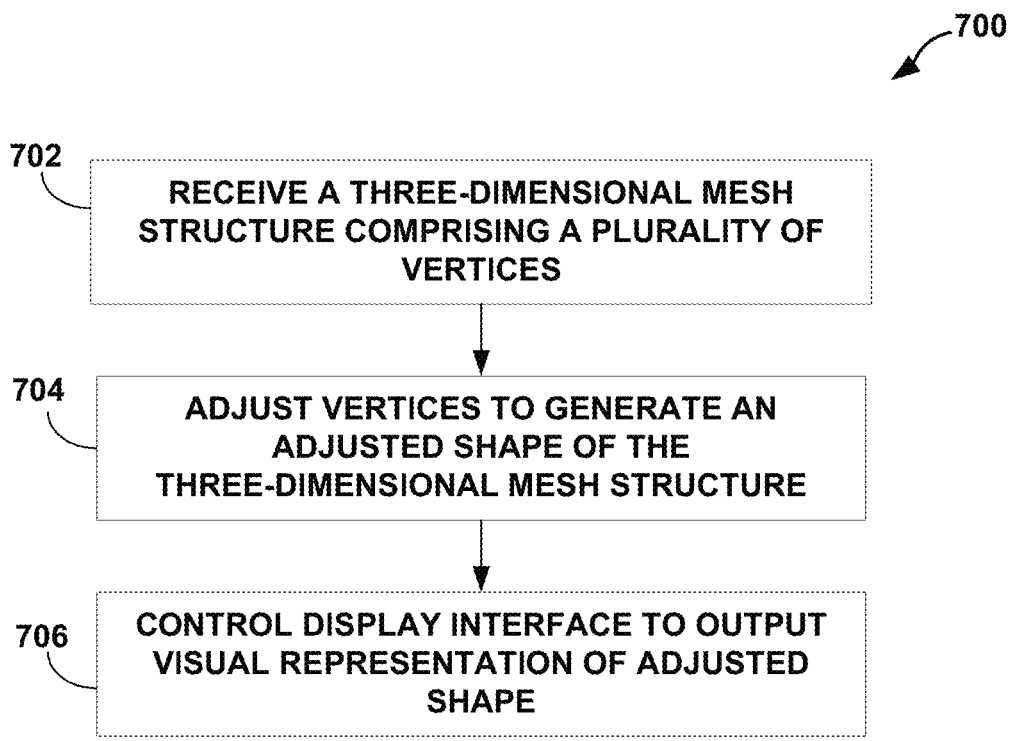
FIG. 7 is a flow diagram illustrating example operation of the computing device of FIG. 2.

FIG. 7 is a flow diagram illustrating an example technique for rendering a visual representation of a VOA using a 3-D mesh structure (700). As shown in FIG. 7, processing circuitry may receive a 3-D mesh structure comprising a plurality of vertices (702). For example, processing circuitry may receive a 3-D mesh structure associated with a plurality of electrodes of a lead. In some examples, the 3-D mesh structure includes a plurality of vertices corresponding to locations on the 3-D mesh structure. For example, the 3-D mesh structure may be stored in memory as vertices coordinates that define a single 3-D mesh structure. In some examples, the 3-D mesh structure may be defined by geometrical data such as height or radius information. For example, texture memory 10 may store data for a cylindrical 3-D mesh structure as height and radius information. In some examples, graphics processor 2 may adjust the geometrical data parameter, such as by increasing the size of the 3-D mesh, upon receiving the 3-D mesh structure according to various parameters. For example, graphics processor 2 may receive information from CPU 88 that the lead geometry is of a certain length, width, etc. and may initially scale the 3-D mesh structure accordingly prior to adjusting vertices in accordance with stimulation parameter data. In some examples, processing circuitry may receive the 3-D mesh structure from a memory look-up operation, from a network, or from a user via UI 98.

In some examples, processing circuitry, such as for CPU 88 or graphics processor 2, may generate 2-D slices, or in some instances 3-D slices, using the 3-D mesh structure in order to determine vertex information. For example, graphics processor 2 may segment the 3-D mesh structure at multiple locations of the structure. As such, the 3-D mesh structure may be divided into rings and/or segments creating vertices across the mesh structure. In some examples, graphics processor 2 may determine multiple vertices along the length of the 3-D mesh structure corresponding to coordinates at which the generated slices intersect the mesh structure. In some instances, graphics processor 2 may store vertex coordinates in graphics memory 8 and/or in system memory 90. Graphics processor 2 may generate slices of the mesh structure according to various memory constraints of the available memory device or devices. That is, graphics processor 2 may generate a number of vertices using 2-D or 3-D slices that coincides with or is at least less than the amount of available memory space in the memory device(s) (e.g., buffer object memory 12, texture memory 10, system memory 90, etc.) allocated to storing vertex information.

In some examples, graphics processor 2 may determine the initial vertex locations of an initial 3-D mesh structure based on a model of a voltage potential field. The model of the voltage potential field may initially be stored in graphics memory 8 as a 3-D voxel grid. In some examples, graphics processor 2 may slice the 3-D voxel grid of the voltage field in order to establish 2-D slices, or in some cases 3-D slices, through the voltage field. For example, graphics processor 2 may establish slices through the voxel grid at locations corresponding to respective contacts (e.g., electrodes) along lead 14. In examples involving ring electrodes 40, graphics processor 2 may establish one slice through the voxel grid for each electrode.

In some examples, lead 14 may include a segmented lead having segmented electrodes. In such instances, graphics processor 2 may generate multiple 2-D slices of electrical field data corresponding to each segmented electrode. These 2-D slices may intersect to form a line coinciding with the longitudinal axis of lead 14, for example. In other examples, the 2-D slices may be parallel to each other and not intersect. In one example, graphics processor 2 may generate a 2-D slice for each segmented electrode. In some examples, graphics processor 2 may establish multiple slices through the voxel grid for each contact and that corresponds to each contact (e.g., electrode). For example, graphics processor 2 may establish multiple slices through the voxel grid at each single level of lead 14 having segmented electrodes 40. In one example for accomplishing such establishment of multiple slices at a single segmented electrode level of lead 14, graphics processor 2 may rotate the slices to align with different angular positions of the level of lead 14 per electrode 40 contact on lead 14 (e.g., one slice per segmented electrode. In one illustrative example involving six electrode segments of lead 14, graphics processor 2 may form six slices through the voltage potential field voxel grid spaced 60 degrees apart with respect to the angular position of that level of lead 14. Graphics processor 2 may rotate the electrical field model 60 degrees in order to establish each slice 360 degrees around lead 14. That is, graphics processor 2 may determine the number of degrees times the number of slices that would be used to cover the span of segments around lead 14, assuming the segmented portion spans 100% or 360 degrees around lead 14. In some instances, the segmented portion may not span 100% of lead 14, in which case the number of degrees of rotation may be adjusted accordingly.

In such examples involving segmented leads, graphics processor 2 may interpolate between each slice in order to determine the voltage potentials at other points in 3-D space around lead 14. For example, graphics processor 2 may form a slice through the voxel grid for each segment of a segmented lead. Graphics processor 2 or CPU 88 may then perform interpolation techniques using the established slices through the electrical field model (e.g., voltage potential voxel grid), to interpolate voltage potentials for any point in 3-D space that surrounds lead 14.

As such, graphics processor 2 may perform vertex adjustments and generate an adjusted shape for multiple 3-D mesh structures that correspond to each slice. That is, graphics processor 2 may perform the process of FIG. 7 multiple times for each slice corresponding to individual segments. In some examples, graphics processor 2 may combine multiple adjusted shapes of 3-D mesh structures to form a single 3-D mesh structure visually representing the VOA for an entire segmented lead.

In some examples, CPU 88 may perform an initial determination as to an estimated VOA shape using tissue activation information, physiological parameters, patient anatomy data, electrode array geometry, etc. For example, CPU 88 may determine that a VOA will likely appear mostly cylindrical with various concavities at various points of the VOA. In some examples, CPU 88 may transmit shape estimation information to graphics processor 2, such that graphics processor 2 may identify a shape and size for the 3-D mesh structure (e.g., mostly cylindrical, partially spherical at one or both ends of a cylinder, etc.) configured to envelope the VOA shape estimation and ultimately, conform to the VOA data.

In addition, CPU 88 may transmit a suggested size of the mesh structure, such that the mesh structure initially envelopes the VOA prior to graphics processor 2 performing vertex adjustments. For example, graphics processor 2 may load from graphics memory 8 a cylindrical mesh structure that has an initially large size, such that graphics processor 2 may shrink wrap the mesh structure to fit the VOA. In some examples, the shape of the mesh structure may be a hollow 3-D structure, such that an inner portion of the 3-D structure coincides with the lead geometry. In such instances, vertices may be slid inward radially toward the outer portion of the VOA and outward radially from the hollow portion of the mesh in order to account for various concavities or irregularities in the VOA.

In any event, graphics processor 2 may determine a size of the mesh structure, for example, by applying a scaling factor to a previously stored mesh structure, such that the size of the mesh structure extends at least beyond the extremities of the energized electrodes of a lead. For example, CPU 88 may provide details regarding electrode energizations to graphics processor 2, including highest point and lowest point energized electrodes along the length of given lead having positioned high point electrodes, middle electrodes, and low point electrodes, where some or all of the electrodes may be energized along the length of lead 14.

In some examples, processing circuitry may adjust the vertices to generate an adjusted shape of the 3-D mesh structure (704). For example, graphics processor 2 may adjust the vertices of the segmented mesh structure to generate an adjusted shape of the mesh structure according to an intersection between activated tissue and non-activated tissue defined by one or more stimulation parameter values. For example, each vertex may be slid radially inward until each vertex rests at the intersection between activated and non-activated tissue as defined by various input settings for the electrical stimulation. For example, the z-axis may be defined as extending longitudinally along the length of lead 14. As such, graphics processing may adjust the x and y coordinates, which slide the vertices radially inward toward the lead. In an illustrative example, graphics processor 2 may access tissue activation data from graphics memory 8. As such, graphics processor 2 may utilize one or more vertex shader(s) 4, such as an OpenGL shader or other shader program, to adjust the vertices of the 3-D mesh structure according to tissue activation data, electrical field data, stimulation template data, etc. Although the vertices are adjusted, the processing circuitry may not need to redraw the entire mesh, which conserves processing resources and time.

In some examples, graphics processor 2 may receive tissue activation data from the CPU 88. For example, graphics processor 2 may receive tissue activation data defining an intersection between activated tissue and non-activated tissue, the tissue activation data based on stimulation parameter values and/or electrical field data. In such examples, graphics processor 2 may store the tissue activation data to a graphics texture memory location. Graphics processor 2 may utilize the tissue activation data to adjust vertices of the single mesh structure radially inward in order to graphically render a visual representation of the VOA. That is, graphics processor 2 may utilize a single 3-D mesh structure, such as a single cylindrical mesh structure, to model different VOAs (e.g., multiple tissue and/or neural activations regions). In some examples, the single 3-D mesh structure may comprise a cylindrical portion and/or an at least partially spherical portion, such as a pill capsule shape.

In some examples, graphics processor 2 may adjust the vertices of the segmented mesh structure based on the tissue activation data stored in texture 10. Graphics processor 2 may manipulate each vertex in parallel, such as to resemble a shrink wrap process. In some examples, graphics processor 2 may manipulate some vertices in parallel, whereas other vertices may be manipulated before or after other vertex adjustments. In some examples, graphics processor 2 may utilize a shader program, such as an OpenGL® shader, to adjust the vertices.

In some examples, processing circuitry, such as processing circuitry of CPU 88, may receive stimulation parameter values that include electrode polarity information. In such examples, CPU 88 may instruct graphics processor 2 to identify data defining a 3-D mesh structure that includes a cylindrical portion and an at least spherical portion. For example, the 3-D mesh structure may include a cylindrical portion that corresponds to one or more electrode cathode locations and the at least partially spherical portion of the 3-D mesh structure corresponds to one or more electrode anode locations. That is, the electric field and/or activation field may include concavities or irregularities that may be modeled using a 3-D mesh structure that takes on a particular form in view of the expected field produced by certain electrode polarities.

In some examples, processing circuitry, such as processing circuitry of graphics processor 2, may control display interface 26 to output a visual representation of the adjusted shape (706). For example, processing circuitry may control display interface 26 to output a visual representation of the adjusted shape of the 3-D mesh structure. In some examples, UI 98 may allow a user to view electrodes from different perspectives relative to the lead and/or actuate both axial and rotation control media to select or view electrodes on the lead. In such examples, graphics processor 2 may cause display interface 26 to provide UI 98 including the adjusted shape of the mesh structure or cross-sections of the mesh structure, such that a user may visualize the estimated VOA from different perspectives as the VOA pertains to specific electrode combinations and stimulation programs. For example, the user may rotate a view of the VOA and leads, such that the GPU may rotate the adjusted mesh structure view to match a view of the VOA at the desired perspective view. The user may utilize UI 98 displaying the visual rendering of the estimated VOA to facilitate efficient evaluation, selection and programming of electrode combinations and stimulation programs.

In some examples, UI 98 may support automated guidance techniques that permit guided selection of electrode combinations and parameters. For example, a user may manipulate the visual rendering of the estimated VOA. Graphics processor 2 may process the user input and cause display of a new VOA rendering in accordance with the techniques of this disclosure. For example, graphics processor 2 may adjust the vertices of the 3-D mesh structure based on the user input to alter the VOA to differ from the originally estimated VOA. Processing circuitry, such as that of graphics processor 2, may determine certain electrical stimulation parameter values that would have caused graphics processor 2 to adjust the vertices of a 3-D mesh structure to resemble the altered VOA. Processing circuitry, such as that of CPU 88, may then determine a stimulation program that would provide the electrical stimulation parameter values. In this way, processing circuitry of device 19 may back calculate stimulation parameter values from adjusted vertex information stored in texture memory 10, such as user-defined vertex information in an altered VOA.

In some examples, processing circuitry, such as that of CPU 88 or graphics processor 2, may determine an activated volume of tissue. In some examples, processing circuitry, such as that of CPU 88, may receive user input, via user interface 98, specifying a request for a new or updated stimulation field. Processing circuitry, such as that of CPU 88 or graphics processor 2, may then adjust the vertices according to user-selected parameter values or automatically selected parameter values selected by device 19 or IMD 20 in order to generate an adjusted 3-D mesh shape that matches the requested stimulation field. Processing circuitry, such as that of CPU 88 or graphics processor 2, may generate the adjusted 3-D mesh shape based on a previously adjusted 3-D mesh shape, such that the previously adjusted 3-D mesh shape serves as an initial shape that processing circuitry, such as that of CPU 88 or graphics processor 2, may mutate to match the newly requested stimulation field.

Figure 8:
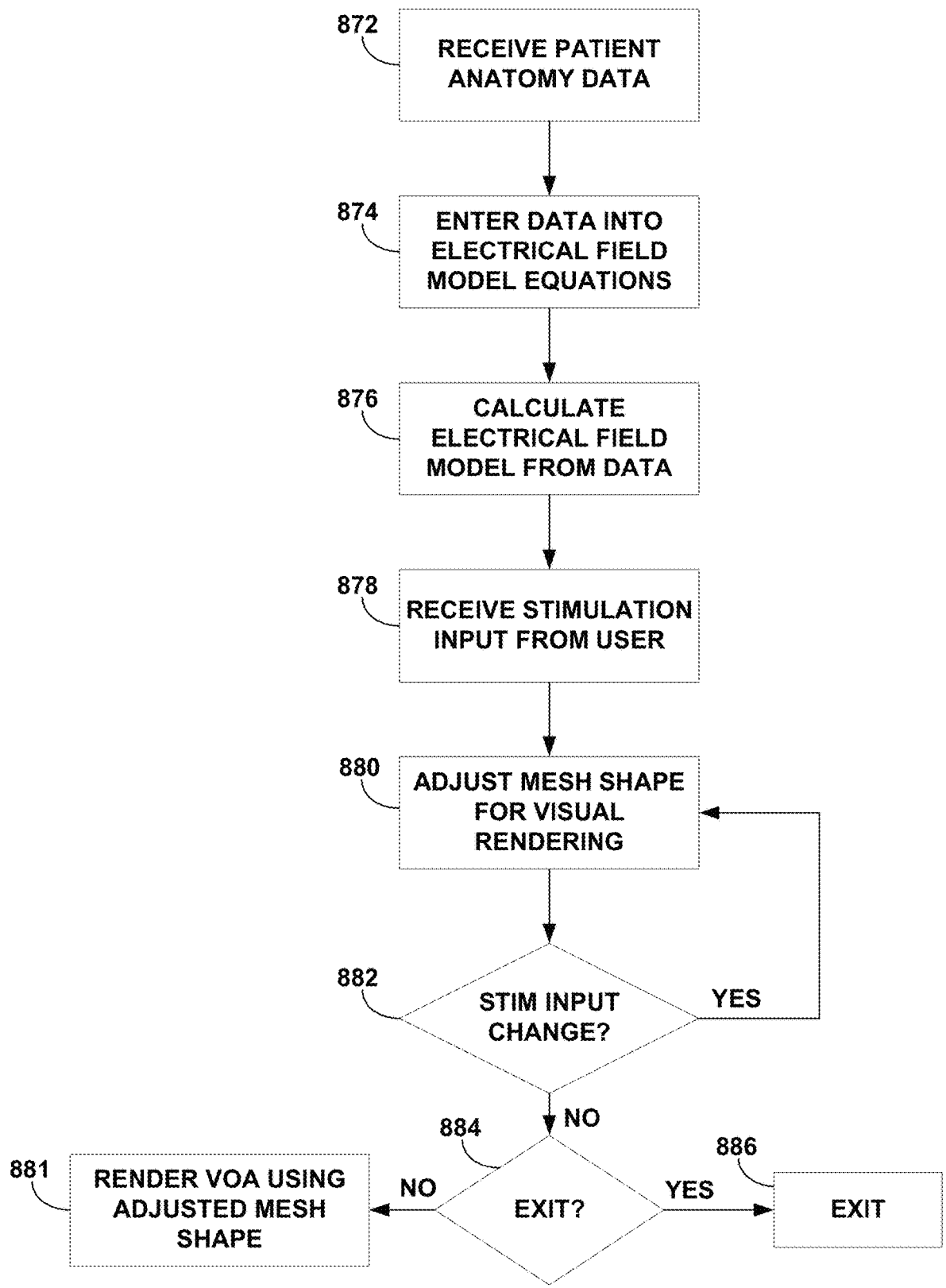
FIG. 8 is a flow diagram illustrating example operation of the computing device for generating and presenting an electrical field model.

FIG. 8 is a flow diagram illustrating an example technique for calculating and displaying the electrical field model of defined stimulation. As shown in FIG. 8, UI 98 receives patient anatomy data for creating an electrical field (872). Device 19 enters the patient anatomy data in stored electrical field model equations or equation sets to satisfy anatomical variable (874). In some examples, device 19 may calculate the electrical field model from the data and equations (876). The electrical field represents where the electrical current will propagate from lead 14, as tissue variation may change the electrical current propagation from the lead in some directions. Device 19 may utilize patient anatomy data with electrical field model equations that define electrical current propagation. More specifically, device 19 may apply the electrical field model equations that define how the electrical field is propagated from an origin location away from the origin. In some examples, the electrical field equations may use the physical tissue characteristics of the tissue adjacent lead 14, which may be included in the patient anatomy data set. This physical tissue characteristics may define a non-homogenous tissue to represent differences in conductivity at different locations from lead 14. In another example, the physical tissue characteristics may be a uniform conductivity model in which the tissue conductivity is modeled the same for all locations from lead 14. From this information, device 19 is able to generate estimated electrical field data.

In some examples, an electrical field model may include general tissue characteristics not specific to patient 50. In some examples, the electrical field equations may utilize matrices or other mathematical models of the electrical field. In this manner, electrical field can be estimated and modeled for the physician. Accordingly, the physician may be able to increase or decrease the amplitude of the stimulation parameters to change the size and/or shape of the electrical field or in some instances, the physician may manipulate the electrical field directly. If the user is satisfied with an electrical field, the user may select an accept field button to transmit the stimulation parameters to IMD 20. In addition, device 19 may generates stimulation parameters from a stimulation field and generate an electrical field model that estimates the electrical field.

In any event, the electrical field model may be rendered graphically and displayed as an electrical field, within a stimulation field. That is, once UI 98 receives stimulation input from the physician defining the stimulation field (878), device 19 may adjust one or more 3-D mesh shapes to conform to the stimulation field and/or the electrical field for subsequent visual rendering, as described in FIG. 7 (880). In some instances, UI 98 may receive a change in the stimulation input ("YES" branch of block 882). For example, a physician may desire to change the stimulation, or the stimulation may change by automatic operation. In such instances, processing circuitry, such as that of CPU 88 or graphics processor 2, may then adjust the mesh shape, or adjust a new mesh shape, for visual rendering based on the stimulation input change (880).

If the physician does not request a stimulation input change ("NO" branch of block 882), processing circuitry, such as that of CPU 88 or graphics processor 2, may render the VOA using the adjusted mesh shape (881). That is, UI 98 may continue to display the VOA. In some examples, UI 98 receives a decision to exit a rendering program ("YES" branch of block 884). Processing circuitry, such as that of CPU 88, may then exit the rendering program (886).

Figure 9:
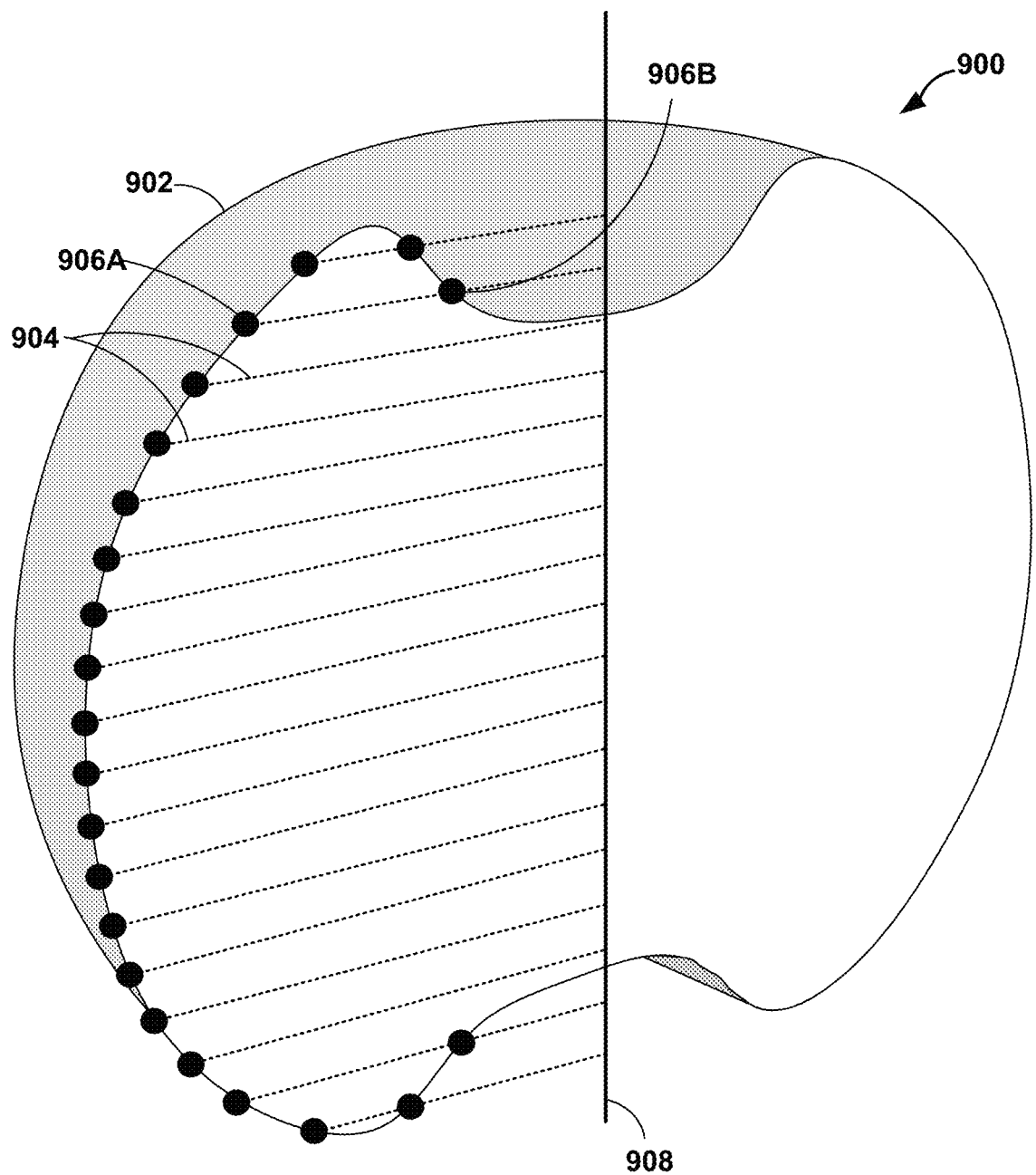
FIG. 9 is a conceptual diagram illustrating example vertex positions of a 3-D mesh structure.

FIG. 9 is a conceptual diagram illustrating example vertex positions of a 3-D mesh structure 900. Mesh structure 900 is an example representation of a 3-D mesh structure having vertices 906 that are moved radially inward to visually represent an estimated VOA 902. In an illustrative example of FIG. 9, 3-D mesh structure 900 may have started out as a mostly cylindrical shape with concavities at both ends of the cylinder. Graphics processor 2 may segment the 3-D mesh as shown by 2-D slices 904 (e.g., the dotted parallel lines). The number of slices 904 may be as many slices as the available memory in graphics memory 8 can support. In some examples, slices 904 may at least coincide with the number of ring electrodes, or the number of levels of segmented electrodes. In other examples, a slice may be provided to intersect each electrode and the space between adjacent electrodes.

As such, graphics processor 2 may slide the vertex position 906A radially inward (from left to right in FIG. 9) according to an intersection between activated and non-activated tissue defined by one or more stimulation parameter values, whereas vertex 906B may slide radially outward (from right to left in FIG. 9) in order to approximate VOA 902 for visual representation and rendering via display 28. Since the radius of mesh structure 900 is symmetrical at any given axial location, each vertex may correspond to the radius around the entire mesh structure 900 at that axial position. This may hold true for ring electrodes and/or when all circumferential electrodes are activated with a common polarity. In situations where mesh structure 900 represents different electrodes at different circumferential positions around the perimeter of the lead, multiple vertices may be provided for the mesh structure 900 at respective circumferential locations in order to adjust the mesh structure 900 for active or inactive electrodes around the circumference.

In the example of FIG. 9, lead 14 (not explicitly shown) may be included along an axis, such as the axis represented by solid line 908. Axis line 908 may go through the center of mesh structure 900. In some examples, the coordinates of vertices 906 may be measured with respect to axis line 908. That is, the coordinates of vertices 906 may include a distance from axis line 908 representing the center of mesh structure 900, such that the vertices may be moved radially inward our outward away from axis line 908 in generating a visual representation of estimated VOA 902. Axis line 908 may be a virtual or invisible line that provides a reference for adjustment of vertices 906. While a vertical line is shown in the example of FIG. 9, the techniques of this disclosure are not so limited, and a person skilled in the art will understand vertical axis line 908 is used as a visual representation to illustrate how vertices 906 may be adjusted in some examples where vertices are slid inward toward a reference point or line or outward away from a reference point or line. In addition, it will be understood that axis line 908 may comprise a series of points that are arranged to form reference points along a linear path. In some instances, the series of reference points may be arranged along a non-linear path, such as in examples where electrodes of lead 14 protrude from lead 14 so as to cause lead 14 to have a less linear structure. The coordinates of reference axis 908 and/or vertices 906 may be arranged so to at least partially conform to the shape of lead 14. For example, lead 14 may comprise a single spherical electrode (not shown), in which case the axis line 908 may form a sphere. Vertices 906 may be adjusted inward toward the sphere axis line 908 or away from the sphere axis line 908.

Figure 10:
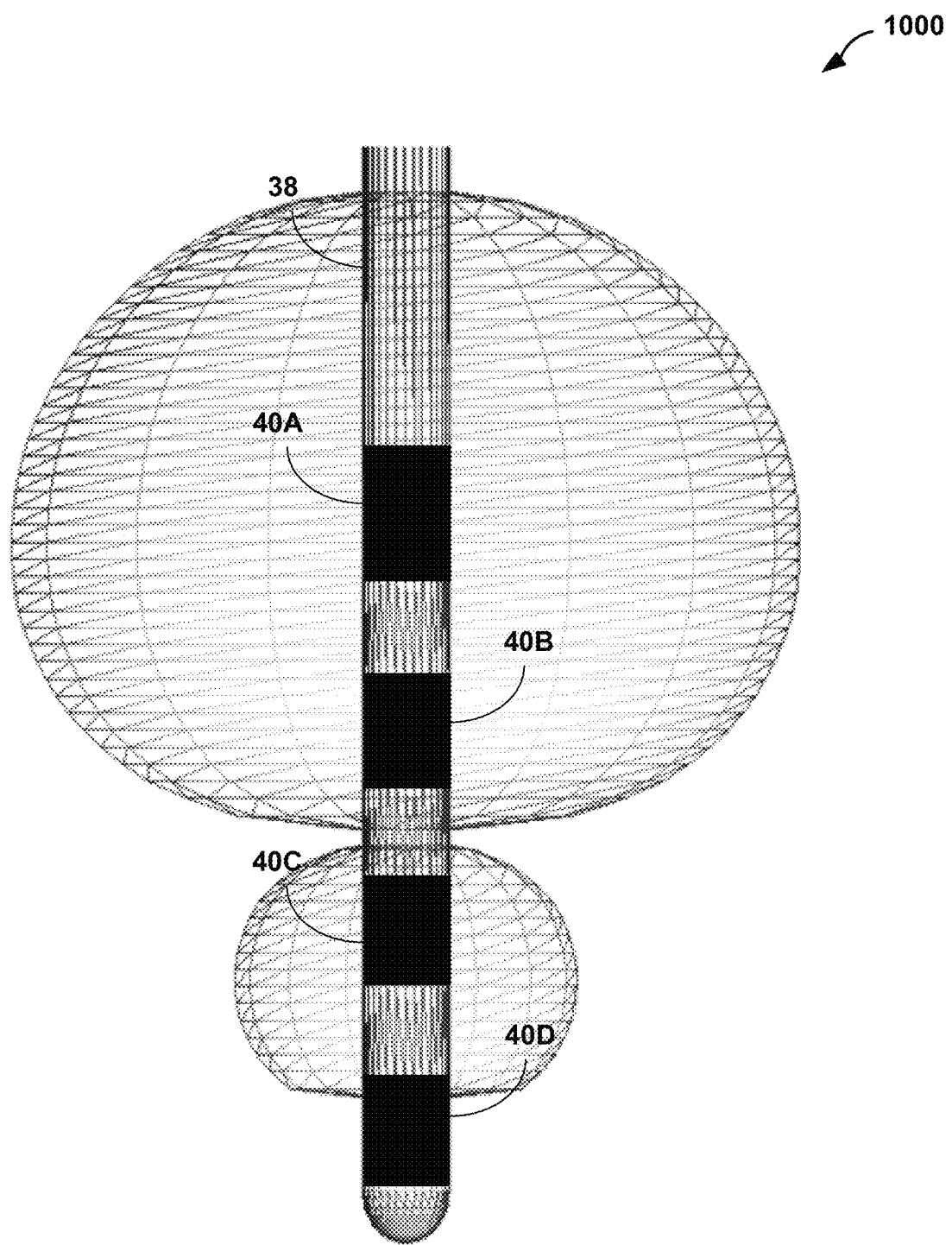
FIG. 10 is a conceptual diagram illustrating one or more example cylindrical mesh structures conformed to an estimated VOA in accordance with one or more techniques of this disclosure.

FIG. 10 is a conceptual diagram illustrating one or more example cylindrical mesh structures conformed to an estimated VOA 1000 in accordance with one or more techniques of this disclosure. As an illustrative example, FIG. 10 illustrates lead 14 of FIG. 5 producing a VOA that generally resembles a sphere or ovoid shape. Regardless the initial 3-D mesh structure may be other shapes. In the example of FIG. 10, the 3-D mesh structure may be cylindrical, where graphics processor 2 radially slides in each vertex to generate an adjusted shape that is now spherical due to the activated tissue and non-activated tissue intersection in this particular example having a spherical shape. In some examples, graphics processor 2 when adjusting the vertices, may adjust at least two of the vertices in parallel with one another. Furthermore, FIG. 10 illustrates two VOAs. In such examples, graphics processor 2 may use a single 3-D mesh structure to graphically model each VOA or may use multiple mesh structures, such as one 3-D mesh structure for each respective finite section of lead 14. Graphics processor 2 may determine such sections based on stimulation parameter values. As such, graphics processor 2 may adjust vertices of each structure in parallel or may adjust vertices for one 3-D mesh structure at a time.

Figure 11:
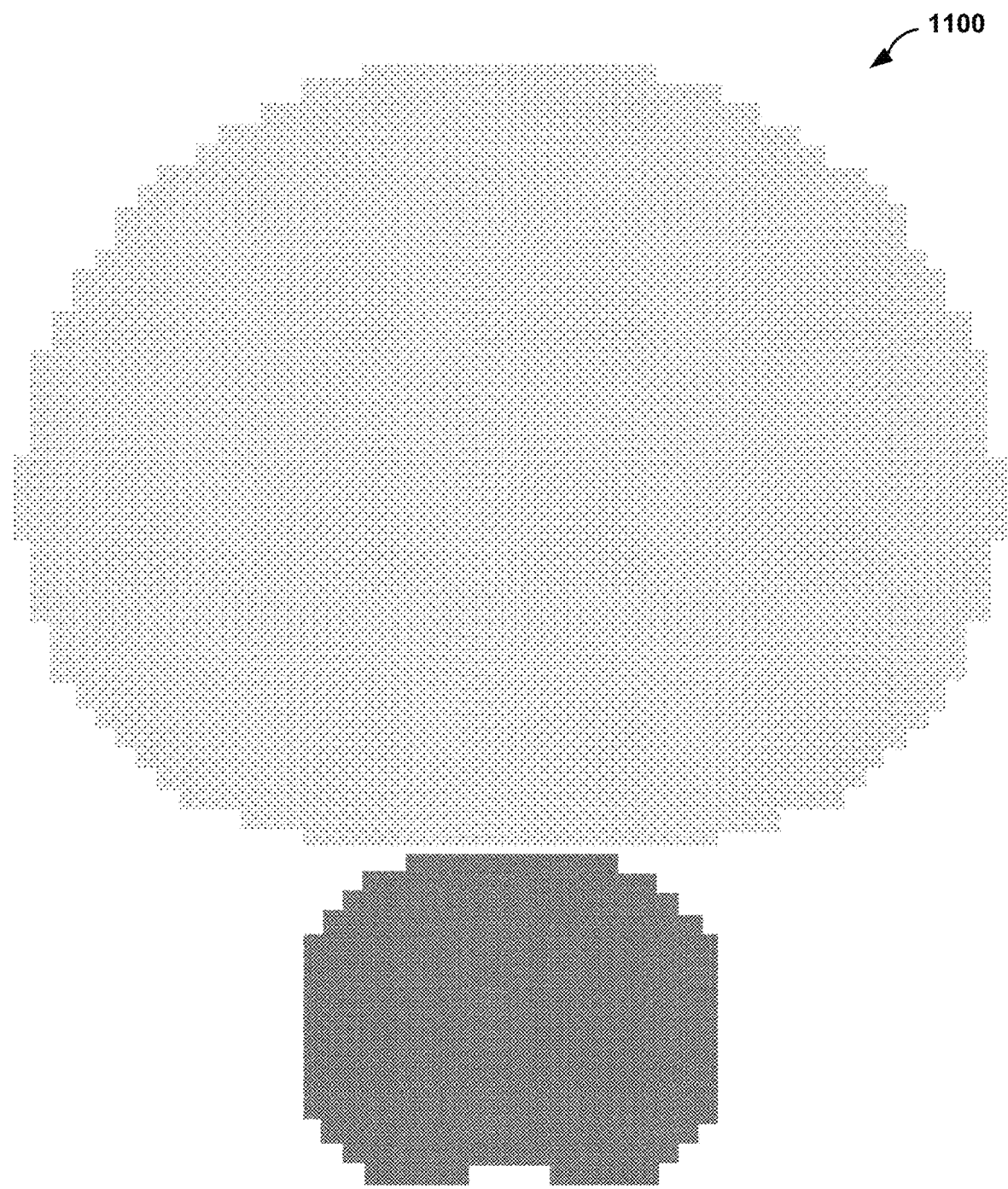
FIG. 11 is a cross-sectional view of an example neural activation map rendered in accordance with one or more techniques of this disclosure.

FIG. 11 is a cross-sectional view of an example VNA 1100 rendered in accordance with one or more techniques of this disclosure. For example, VNA 1100 may correspond to electrical stimulation parameters used to generate the VOA shown in FIG. 10. As such, graphics processor 2 may generate VNA 1100 using 3-D mesh structures having vertices adjusted in accordance with neuron models and/or electrical field models as described herein. The cross-sectional view may provide a cross-section of a 3-D map. The 3-D map may be rotated based on input received via user interface so as to view other cross-section of the 3-D map.

Figure 12:
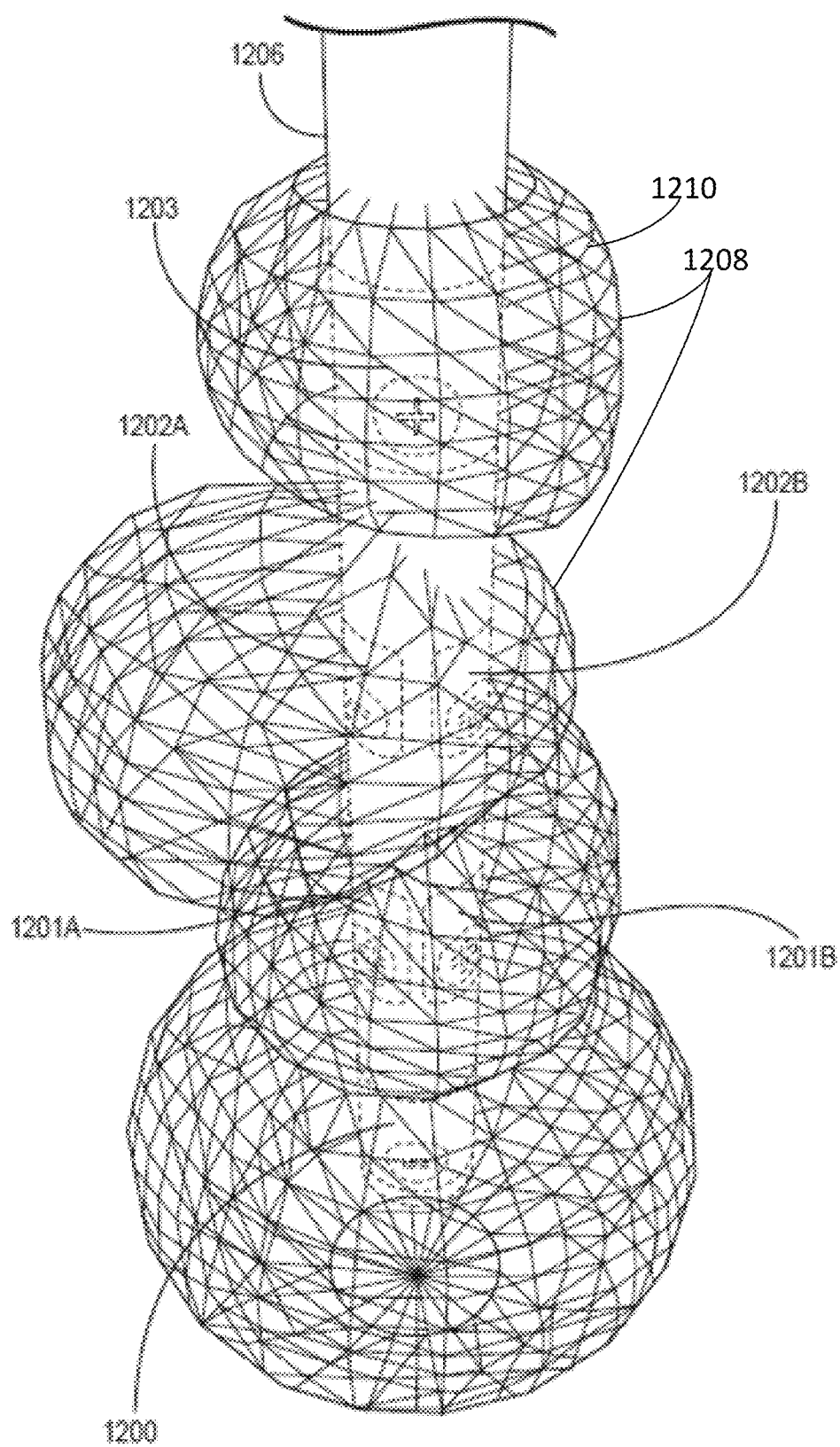
FIG. 12 is a conceptual diagram illustrating example 3-D mesh structures having adjusted vertex positions in accordance with one or more techniques of this disclosure.

FIG. 12 is a conceptual diagram illustrating example 3-D mesh structures 1208 having adjusted vertex positions in accordance with one or more techniques of this disclosure. FIG. 12 shows an example segmented lead 1206 having electrode segments and ring electrodes. In the example of FIG. 12, lead 1206 has a first level having a ring electrode 1203. In addition, lead 1206 has a second and third level having electrodes 1202A, 1202B, 1201A, and 1201B illustrating segmented electrodes of the lead. In the example of FIG. 12, lead 1206 has additional electrodes on the opposite side of lead 1206 that cannot be seen in the particular view orientation of FIG. 12. For example, the electrode level having electrodes 1202A and 1202B would have a third electrode on the opposite side of lead 1206 that cannot be seen in the particular view of FIG. 12. Likewise, the electrode level having electrodes 1201A and 1201B would have a third electrode on the opposite side of lead 1206 that cannot be seen in the particular view of FIG. 12. Lastly, another ring electrode 1200 is shown toward the end of lead 1206. In addition, FIG. 12 illustrates cathode (−) and anode (+) polarities of various electrodes of lead 1206. With this lead configuration and under certain stimulation parameters, graphics processor 2 is configured to manipulate the vertices of multiple 3-D mesh shapes around the energized electrodes in accordance with one or more techniques of this disclosure. FIG. 12 illustrates the vertices of multiple 3-D mesh structures 1208 manipulated inward at respective locations from an initial 3-D mesh structure (e.g., a cylindrical shaped 3-D structure) that wraps around, for example, regions of tissue activation defined by stimulation parameter values, electrical field data, etc.

In some examples, graphics processor 2 may smooth the 3-D mesh structure or structures 1208, for example, by including gradient shadows or colors to illustrate dimensional aspects of adjusted shape. In addition, graphics processor 2 may remove the slice lines 12010 and vertices shown in FIG. 12. A user may toggle between a view having lines 1210 throughout the adjusted shape to a view having the adjusted shape without and slice lines 1210. In one example, graphics processor 2 may render, via display interface 26, the adjusted 3-D mesh shape 1300 by manipulating vertices of the 3-D mesh shape inward along slices of an electrical potential field model from initial vertex positions until the vertices align with the threshold of the VOA as determined, for example, from stimulation parameter values, electrical field data, and/or tissue activation data. For illustrative purposes, FIG. 12 illustrates a visual of a 3-D mesh representing a VOA estimated from a first set of stimulation parameters and where vertices of the 3-D mesh structure have been adjusted accordingly to create the adjusted shape.

Figure 13:
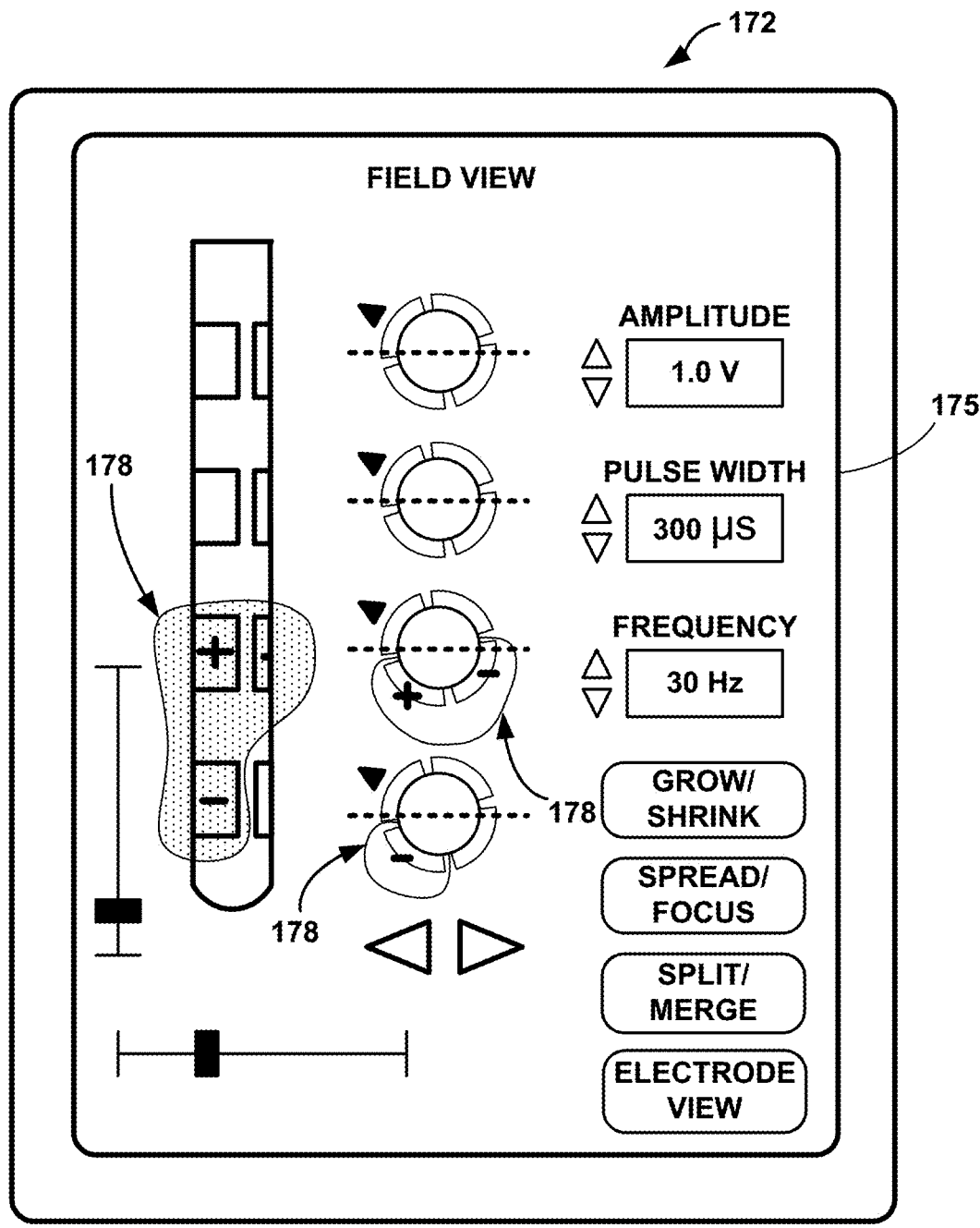
FIG. 13 is a schematic diagram illustrating an example user interface presented by the computing device of FIG. 1.

In some examples, electrical stimulation parameters may be automatically suggested from a desired stimulation region. In such instances, an estimated VOA rendering may be generated to illustrate how the estimated VOA would look based on the electrical stimulation parameters. For example, FIG. 13 illustrates a UI 172 that presents field view 175 of lead 14. In some examples, UI 172 may present multiple cross-sectional views of lead 14 in alignment with corresponding electrode levels of lead 14. In the example of FIG. 13, the user has selected an initial electrode combination, such as through UI 150 of FIG. 4, and has transitioned to a field view of the electrode combination. In the field view, UI 172 presents a representation of a stimulation field 178 defined by the user and produced by the electrode combination, given the parameter values associated with stimulation delivered by the electrode combination and general tissue characteristics. The size and shape of stimulation field 178 may be established based on generic physical characteristics of human tissue and known physical characteristics of the electrodes of lead 14. In such instances, processing circuitry, such as that of CPU 88, may automatically determine electrical stimulation parameters from a desired stimulation region defined by UI 172.

In such examples, graphics processor 2 may render stimulation field 178 in accordance with one or more techniques of this disclosure. For example, graphics processor 2 may apply a 3-D mesh structure, such as a cylindrical mesh structure, to fit the stimulation field by adjusting vertices of a 3-D mesh structure radially inward to stimulation field 178. The stimulation field 178 may be displayed, via UI 172, in relation to lead 14 as rendered based on the adjusted shape of the 3-D mesh structure, adjusted in accordance with various techniques of this disclosure. As such, graphics processor 2 may control display interface 26 to output the adjusted shape to display 28 via UI 172 (e.g., an example user interface 98 or an example user interface 150).

Figure 14:
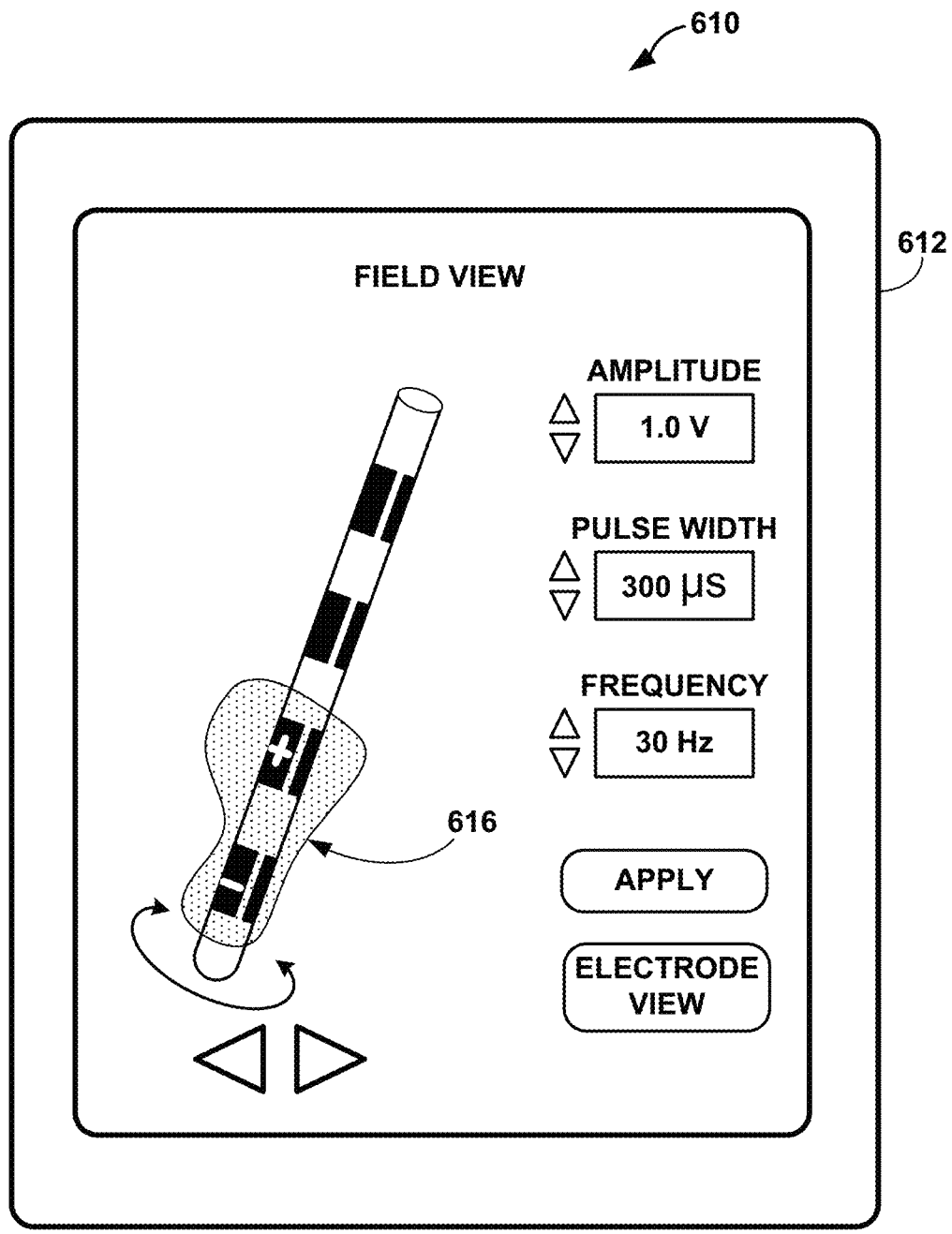
FIG. 14 is a diagram illustrating a user interface presenting a 3-D field view with respect to the lead of FIG. 1.

In another example, FIG. 14 is a diagram illustrating a user interface 610 presenting a 3-D view of an estimated VOA with respect to lead 14 and stimulation field 616. Although some examples include presentation of 2-D views of lead 14 and the estimated VOA, a 3-D rendering may also be useful. Stimulation field 616 may be shown with respect to patient anatomy and/or lead 14. User interface 610 is an example of UI 98 and programmer 612 is an example of device 19. In such examples, graphics processor 2 may render a 3-D view of the lead, such as an isometric view, using techniques in accordance with one or more techniques of this disclosure. For example, graphics processor 2 may determine an adjusted 3-D shape of a 3-D mesh structure by manipulating vertices of the segmented mesh structure, where the vertices may be adjusted to fit stimulation field 616 and/or to fit lead 14 and electrodes. In some examples, graphics processor 2 may store the adjusted 3-D shapes in graphics memory 8 or in some instances, system memory 90. As such, graphics processor 2 may then render a virtual 3-D view of the stimulation field and/or of the lead and electrodes.

Although this disclosure has referred to stimulation applications generally, and DBS and SCS applications more particularly, such applications have been described for purposes of illustration and should not be considered limiting of the disclosed technology, as described herein. The disclosed technology may be more generally applicable to rendering for display regions of activation, such as nerve tissue or muscle tissue activation regions, and may be applicable in a variety of contexts including visual rendering of spinal cord stimulation, pelvic floor stimulation, deep brain stimulation, cortical surface stimulation, neuronal ganglion stimulation, gastric stimulation, peripheral nerve stimulation, or subcutaneous stimulation. Also, the disclosed technology is not necessarily limited to visual renderings with respect to implanted stimulators, and may also be applicable in the context of external stimulators coupled to implanted leads, e.g., via a percutaneous port. In addition, the disclosure may be applicable to a wide variety of electrode array geometries including virtually any number of axial and angular electrode positions.

In addition, electrode array geometries may include arrays of electrodes positioned at different axial positions along the length of a lead, as well as at different angular positions about the circumference of the lead. In some examples, the electrodes may appear similar to non-contiguous, arc-like segments of a conventional ring electrode. A lead with a complex electrode array geometry may include multiple rings of electrode segments. Each axially positioned ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section. Also, electrodes positioned at particular axial or angular positions need not be aligned with other electrodes. Rather, in some examples, electrodes may be arranged in a staggered or checkerboard-like pattern.

Further, although a single lead may be useful in various stimulation applications, multiple leads may be useful in other applications such as bi-lateral DBS, SCS, or multi-site stimulation for gastric, pelvic or peripheral nerve stimulation. Accordingly, electrode combinations may be formed between electrodes carried by a single lead, electrode combinations formed between electrodes carried by one lead of a pair of leads, or electrode combinations formed between electrodes on different leads, as well as electrodes carried by a stimulator housing.

The techniques described herein may be applied to a programming interface or control interface associated with a physician programmer, a patient programmer, or both. Hence, a physician may use a physician programmer in clinic to program and evaluate different electrode combinations and stimulation parameter values. A patient may use a patient programmer during daily use to adjust parameter values and select different electrode combinations. The physician programmer or patient programmer may be a small, portable, handheld device, similar to a smartphone or tablet device. In some examples, a programmer may be implemented in a general-purpose desktop or laptop computer, computer workstation, or dedicated desktop programming unit.

In addition, the programming functionality described in this disclosure may be used to program a stimulator coupled to one or more implantable leads or an external stimulator coupled to one more percutaneous leads. In addition, the evaluation techniques provided by device 19 may be used in a physician programmer or patient programmer.

The physician programmer, patient programmer or both may include the ability to present both an electrode view for manual selection of electrodes and parameter values, and a field view for manipulation of stimulation field size, position or shape followed by automatic programming of electrode combination and parameter values to approximate the desired stimulation field. The stimulation field may be defined by the selected stimulation parameters in the electrode view or by outlining and defining the stimulation field first. The stimulation field may be manipulated by a variety of input media, including soft keys, touchscreen keys, hard keys, scroll wheels, touchpads, joysticks, a mouse, a trackball, or other devices.

In general, such input devices may be used to provide different viewing perspectives (e.g., side, cross-sectional, concentric axial, unwrapped 2D array, etc.) of a lead, and permit rotation of the perspective views to observe sides of the lead that may not be visible in a single two-dimensional side view. Other perspective view, independent or in conjunction with axial and cross-sectional views, are possible. For example, skewed views looking down the length of the lead from above are possible. In addition, views showing both sides of a lead are possible.

The techniques described in this disclosure may be implemented, at least in part, in hardware, software, firmware or any combination thereof. For example, various aspects of the described techniques may be implemented within one or more processors or processing circuitry, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure. In an illustrative example, processing circuitry of device 19 may include graphics processor 2 and/or CPU 88 hardware, software, or firmware components, or combinations thereof.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include RAM, ROM, PROM, EPROM, EEPROM, flash memory, a hard disk, a CD-ROM, a floppy disk, a cassette, magnetic media, optical media, or other computer readable media.

Various examples of the disclosed technology have been described. These and other examples are within the scope of the following claims.

What is claimed is:

1. A method comprising:
   receiving, by a graphics processing unit (GPU), a three-dimensional mesh structure associated with a plurality of electrodes of a lead and generated by a central processing unit (CPU) different from the GPU;
   receiving, by the GPU, tissue activation data defining an intersection between activated tissue and non-activated tissue;
   automatically adjusting, by the GPU, a relative location of one or more vertices of the three-dimensional mesh structure toward the intersection between the activated tissue and the non-activated tissue to generate an adjusted shape of the three-dimensional mesh structure according to the intersection between the activated tissue and the non-activated tissue; and
   controlling, by the GPU, a display interface to output a visual representation of the adjusted shape of the three-dimensional mesh structure.

2. The method of claim 1, wherein the three-dimensional mesh structure comprises a plurality of vertices corresponding to respective locations on the three-dimensional mesh structure, the plurality of vertices comprising the one or more vertices.

3. The method of claim 2, further comprising:
   identifying, by the GPU, the three-dimensional mesh structure;
   segmenting, by the GPU, the three-dimensional mesh structure to determine the plurality of vertices; and
   storing the plurality of vertices to a location in graphics memory, and
   wherein receiving the three-dimensional mesh structure further comprises:
     receiving the plurality of vertices from the location in graphics memory.

4. The method of claim 2, wherein adjusting the relative location of the one or more vertices of the plurality of vertices comprises adjusting at least two vertices of the plurality of vertices in parallel with one another.

5. The method of claim 1,
   wherein the tissue activation data is based on at least one of one or more stimulation parameter values or electrical field data, and wherein the method further comprises:
     storing, by the GPU, the tissue activation data to a location in graphics memory.

6. The method of claim 5, further comprising:
   accessing the tissue activation data from the graphics memory; and
   adjusting, via a vertex shader, the relative location of the one or more vertices according to the tissue activation data.

7. The method of claim 1, wherein the three-dimensional mesh structure comprises a single mesh configured to model a plurality of different activated tissue regions.

8. The method of claim 1, further comprising:
   storing, by the GPU, data defining the three-dimensional mesh structure to a location in graphics memory.

9. The method of claim 1, wherein the three-dimensional mesh structure comprises at least one of: a cylindrical portion or an at least partially spherical portion.

10. The method of claim 9, further comprising:
    receiving, by the GPU, one or more stimulation parameter values,
    wherein the one or more stimulation parameter values comprise electrode polarity information, and
    wherein the cylindrical portion of the three-dimensional mesh structure is configured to correspond to an electrode cathode location and the at least partially spherical portion of the three-dimensional mesh structure is configured to correspond to an electrode anode location.

11. The method of claim 1, wherein the adjusted shape of the three-dimensional mesh structure represents a volume of neural activation (VNA) corresponding to electrical stimulation deliverable by the lead and according to one or more stimulation parameter values.

12. The method of claim 1, wherein the display interface includes a touch screen interface.

13. A computing device comprising:
    a graphics processing unit (GPU) configured to:
      receive a three-dimensional mesh structure associated with a plurality of electrodes of a lead and generated by a central processing unit (CPU) different from the GPU;
      receive tissue activation data defining an intersection between activated tissue and non-activated tissue;
      automatically adjust a relative location of one or more vertices of the three-dimensional mesh structure toward the intersection between the activated tissue and the non-activated tissue to generate an adjusted shape of the three-dimensional mesh structure according to the intersection between the activated tissue and the non-activated tissue; and
      control a display interface to output a visual representation of the adjusted shape of the three-dimensional mesh structure.

14. The computing device of claim 13, wherein the three-dimensional mesh structure comprises a plurality of vertices corresponding to respective locations on the three-dimensional mesh structure, the plurality of vertices comprising the one or more vertices.

15. The computing device of claim 13, wherein
    the tissue activation data is based on at least one of one or more stimulation parameter values or electrical field data, and wherein the GPU is configured to
    store the tissue activation data to a location in graphics memory.

16. The computing device of claim 13, the three-dimensional mesh structure comprises at least one of: a cylindrical portion or an at least partially spherical portion, and wherein the GPU is configured to receive one or more stimulation parameter values,
    wherein the one or more stimulation parameter values comprise electrode polarity information, and
    wherein a cylindrical portion of the three-dimensional mesh structure is configured to correspond to an electrode cathode location and the at least partially spherical portion of the three-dimensional mesh structure is configured to correspond to an electrode anode location.

17. The computing device of claim 13, wherein an external programmer comprises the GPU, graphics memory, and the display interface.

18. The computing device of claim 13, wherein the GPU is configured to:
identify the three-dimensional mesh structure;
segment the three-dimensional mesh structure to determine a plurality of vertices, the plurality of vertices comprising the one or more vertices;
store the plurality of vertices to a location in graphics memory; and
receive the three-dimensional mesh structure by at least receiving the plurality of vertices from the location in the graphics memory.

19. A non-transitory computer-readable storage medium having stored thereon instructions that, when executed, cause a graphics processing unit (GPU) to at least:
receive a three-dimensional mesh structure associated with a plurality of electrodes of a lead and generated by a central processing unit (CPU) different from the GPU;
receive tissue activation data defining an intersection between activated tissue and non-activated tissue;
automatically adjust a relative location of one or more vertices of the three-dimensional mesh structure toward the intersection between the activated tissue and the non-activated tissue to generate an adjusted shape of the three-dimensional mesh structure according to the intersection between the activated tissue and the non-activated tissue; and
control a display interface to output a visual representation of the adjusted shape of the three-dimensional mesh structure.

20. The non-transitory computer-readable storage medium of claim 19, wherein
the tissue activation data is based on at least one of one or more stimulation parameter values or electrical field data, and wherein the instructions further comprise instructions that case the GPU to:
store the tissue activation data to a location in graphics memory.

* * * * *